US011202620B2

(12) United States Patent
Morimoto et al.

(10) Patent No.: US 11,202,620 B2
(45) Date of Patent: Dec. 21, 2021

(54) ULTRASONIC ENDOSCOPE

(71) Applicant: FUJIFILM Corporation, Tokyo (JP)

(72) Inventors: Yasuhiko Morimoto, Ashigara-kami-gun (JP); Katsuya Yamamoto, Ashigara-kami-gun (JP); Satoru Okada, Ashigara-kami-gun (JP)

(73) Assignee: FUJIFILM Corporation, Tokyo (JP)

(*) Notice: Subject to any disclaimer, the term of this patent is extended or adjusted under 35 U.S.C. 154(b) by 392 days.

(21) Appl. No.: 16/235,239

(22) Filed: Dec. 28, 2018

(65) Prior Publication Data
US 2019/0133558 A1 May 9, 2019

Related U.S. Application Data

(63) Continuation of application No. PCT/JP2017/023370, filed on Jun. 26, 2017.

(30) Foreign Application Priority Data

Jun. 30, 2016 (JP) .............................. JP2016-130112

(51) Int. Cl.
*A61B 8/12* (2006.01)
*A61B 8/00* (2006.01)

(52) U.S. Cl.
CPC ................ *A61B 8/546* (2013.01); *A61B 8/12* (2013.01); *A61B 8/445* (2013.01); *A61B 8/4466* (2013.01); *A61B 8/4494* (2013.01)

(58) Field of Classification Search
CPC ........... A61B 8/12; A61B 8/44; A61B 8/4444; A61B 8/445; A61B 8/4483; A61B 8/4488; A61B 8/546; B06B 1/0622
See application file for complete search history.

(56) References Cited

U.S. PATENT DOCUMENTS

2006/0234788 A1* 10/2006 Chuang ............... H04M 1/0202
455/575.7
2006/0241481 A1 10/2006 Itoi
(Continued)

FOREIGN PATENT DOCUMENTS

EP 1 707 125 A1 10/2006
EP 1707125 A1 10/2006
(Continued)

OTHER PUBLICATIONS

International Preliminary Report on Patentability and Written Opinion of the International Searching Authority(Forms PCT/IB/326, PCT/IB/373 and PCT/ISA/237), dated Jan. 10, 2019, for International Application No. PCT/JP2017/023370, with an English Translation of the Written Opinion.

(Continued)

*Primary Examiner* — Mark D Remaly
(74) *Attorney, Agent, or Firm* — Birch, Stewart, Kolasch & Birch, LLP

(57) ABSTRACT

An ultrasonic endoscope includes an ultrasonic vibrator unit provided at a distal end part, the ultrasonic vibrator unit being composed of at least an ultrasonic vibrator array and a first thermally conductive member, the ultrasonic vibrator array having the plurality of ultrasonic vibrators that are arranged in a cylindrical form, the first thermally conductive member being disposed thermally in contact with the ultrasonic vibrator array; a plurality of cables that are electrically connected to the ultrasonic vibrator array; and an electrically conductive structural body that is disposed to extend from a distal end side toward a proximal end side of the ultrasonic endoscope. The ultrasonic vibrator unit and the electrically conductive structural body are connected to each other via an electrically insulating second thermally conductive member. Thus, the ultrasonic endoscope that has a heat release structure which transmits the heat generated from the ultra- (Continued)

sonic vibrator to the electrically conductive endoscopic structure housed in a distal end part and which can efficiently release the heat therefrom while electric safety is secured; and that can prevent a burn of an alimentary canal by suppressing a temperature rise of surfaces of the ultrasonic vibrators is provided.

10 Claims, 11 Drawing Sheets

(56) References Cited

U.S. PATENT DOCUMENTS

| | | |
|---|---|---|
| 2008/0009742 A1 | 1/2008 | Kondoh |
| 2008/0300492 A1 | 12/2008 | Nagano et al. |
| 2008/0306389 A1 | 12/2008 | Nagano et al. |
| 2009/0088646 A1 | 4/2009 | Nagano et al. |
| 2009/0234233 A1 | 9/2009 | Nagano et al. |
| 2014/0046190 A1* | 2/2014 | Ogawa ............... A61B 8/4444 600/462 |
| 2015/0173711 A1* | 6/2015 | Hiraoka ............... A61B 8/4494 600/466 |

FOREIGN PATENT DOCUMENTS

| | | |
|---|---|---|
| GB | 2 258 364 A | 2/1993 |
| GB | 2258364 A | 2/1993 |
| JP | 2006-280407 A | 10/2006 |
| JP | 2008-22077 A | 1/2008 |
| JP | 2008-295749 A | 12/2008 |
| JP | 2008-301893 A | 12/2008 |
| JP | 2009-240755 A | 10/2009 |
| JP | 5329065 B2 | 10/2013 |

OTHER PUBLICATIONS

International Search Report (Form PCT/ISA/210), dated Aug. 8, 2017, for International Application No. PCT/2017/023370, with an English translation.

Sakamoto et al., "Development of Large Size Peltier Module with High Power," Furukawa Electric Review, No. 115, Furukawa Denko Kabushiki Kaisha, 2005, pp. 21-25, 5 pages.

Extended European Search Report, dated Jul. 12, 2019, for European Application No. 17820092.9.

Chinese Office Action and Search Report for Chinese Application No. 201780039481.9, dated Jan. 12, 2021, with an English translation.

* cited by examiner

ULTRASONIC ENDOSCOPE

CROSS-REFERENCE TO RELATED APPLICATIONS

This application is a Continuation of PCT International Application No. PCT/JP2017/023370 filed on Jun. 26, 2017, which claims priority under 35 U.S.C. § 119(a) to Japanese Patent Application No. 2016-130112 filed on Jun. 30, 2016. The above application is hereby expressly incorporated by reference, in its entirety, into the present application.

BACKGROUND OF THE INVENTION

1. Field of the Invention

The present invention relates to ultrasonic endoscopes, and more particularly relates to an ultrasonic endoscope having, at a distal end part thereof, a heat release structure for releasing the heat generated from very small ultrasonic vibrators used in the ultrasonic endoscope that is inserted into a body cavity.

2. Description of the Related Art

An ultrasound diagnostic apparatus using ultrasonic imaging typically includes an ultrasound probe for body surface that is used by being brought into contact with a subject, and an ultrasound probe for body cavity that is used by being inserted into a body cavity of a subject. Furthermore, in recent years, an ultrasonic endoscope is used which is a combination of an endoscope for optically observing the inside of a subject, and an ultrasound probe for body cavity.

When an ultrasound probe transmits an ultrasound beam to a subject such as a human body and receives an ultrasound echo generated from the subject, ultrasound image information is acquired.

Based on the ultrasound image information, an ultrasound image of an object existing in the subject (for example, an internal organ or a lesion tissue) is displayed on a display unit of an ultrasonic endoscope apparatus body that is connected to the ultrasonic endoscope.

A typically used example of ultrasonic transducers (ultrasonic vibrator array) that transmit and receive ultrasonic waves is a plurality of ultrasonic vibrators (piezoelectric vibrators) in which electrodes are formed on both surfaces of a material (piezoelectric body) that exhibits a piezoelectric effect.

When a voltage is applied to the electrodes of the ultrasonic vibrators, the piezoelectric body is expanded and contracted by the piezoelectric effect and ultrasonic waves are generated. The plurality of ultrasonic vibrators are arranged in a one-dimensional form or a two-dimensional form to serve as an ultrasonic vibrator array, and by successively driving the plurality of ultrasonic vibrators, an ultrasound beam that is transmitted in a desirable direction can be formed.

Also, the ultrasonic vibrators are expanded and contracted by receiving propagating ultrasonic waves, and generate electric signals. The electric signals are used as detection signals of ultrasonic waves.

The ultrasonic endoscope including the plurality of ultrasonic vibrators is provided with an ultrasonic observation portion at a distal end part of the endoscope, as a major purpose, to observe the gallbladder or pancreas via an alimentary canal. The distal end part of the ultrasonic endoscope is provided with, in addition to the ultrasonic observation portion, an optical sensor, a light, an air supply port, a water supply port, and a suction port, like a typical endoscope not provided with the ultrasonic observation portion. With such an ultrasonic endoscope that is inserted into a body cavity of a subject, in particular, an upper alimentary canal or a bronchus, it is requested to decrease the diameter of an insertion section of the ultrasonic endoscope, and the size of the distal end part, in particular, the size of the ultrasonic observation portion, to reduce the physical burden of the subject.

Also, the distal end part of the ultrasonic endoscope involves heat generating factors, such as the ultrasonic vibrators and the light source of the endoscope. The insertion section of the ultrasonic endoscope, in particular, the distal end part directly contacts the inside of a living body such as a human body. Hence, for safety reasons such as preventing a moderate-temperature burn, it is demanded to set the surface temperature of the insertion section to a predetermined temperature or lower.

Owing to this, an ultrasonic endoscope that has means for decreasing the surface temperature of the distal end part while the size of the distal end part is held small is requested. In recent years, various suggestions are made for cooling the distal end part of the ultrasonic endoscope that is a heat generation source (see JP5329065B, JP2009-240755A, and JP2008-22077A).

JP5329065B discloses an ultrasonic endoscope including an insertion section having a bending part. The insertion section has a backing material, an exterior member, and a thermally conductive member that is disposed in the exterior member and that contacts a back surface of the backing material and an inner surface of the exterior member. The backing material has a front surface on which a plurality of ultrasonic transducers are disposed. Also, the exterior member is made of stainless steel (SUS) or the like that houses the plurality of ultrasonic transducers at a distal end of the insertion section. With this configuration, the heat generated from the ultrasonic transducers and transmitted to the backing material, and the heat generated from the backing material as the result that the backing material receives ultrasonic waves from the ultrasonic transducers are transmitted to the thermally conductive member via the backing material. Further, the heat transmitted to the thermally conductive member is transmitted to the exterior member via the thermally conductive member, and is released from the exterior member to the outside of the ultrasonic endoscope. Thus, with JP5329065B, the heat release from the ultrasonic transducers to the outside is promoted.

JP2009-240755A discloses an ultrasonic endoscope in which a signal line housing part that is located below a backing material supporting a plurality of ultrasonic transducers and that houses a plurality of signal lines (shield line group) is filled with a highly thermally conductive filling material. Further, with the ultrasonic endoscope, a highly thermally conductive layer such as a copper foil is disposed on a bottom surface, side surfaces, and a rear surface of the signal line housing part. With this configuration, the ultrasonic endoscope of JP2009-240755A efficiently releases the heat generated from the ultrasonic transducers by diffusing the heat to a surface of an exterior material via a backing layer, the highly thermally conductive filling material in the signal line housing part, and the highly thermally conductive layer.

JP2008-22077A discloses an ultrasound probe in which individual metal thin plates, serving as thermally conductive materials, are provided on earth electrode sides of a plurality of piezoelectric elements. With the ultrasound probe, the individual metal thin plates are thermally connected to a heat release base that is located below a backing material that supports the piezoelectric elements, via a common metal thin plate or an electrically insulating thermally conductive material that is joined to an end surface of the backing material. With this configuration, the ultrasound probe of JP2008-22077A releases the heat generated from the piezoelectric elements to the heat release base via the individual metal thin plates, and the common metal thin plate, or the electrically insulating thermally conductive member.

SUMMARY OF THE INVENTION

With the ultrasonic endoscope disclosed in JP5329065B, only a heat release path for releasing the heat generated from the ultrasonic vibrators and the backing material layer to the exterior member via the thermally conductive member is taken into account, and hence it is difficult to further improve the heat release effect. Further, with the technology disclosed in JP5329065B, heat does not stay in the ultrasonic vibrators and the backing material layer;

however, since the heat is released to the exterior member of, for example, SUS, the heat may be released to the inside of the body cavity near the distal end part of the ultrasonic endoscope. In this case, a temperature rise is suppressed by a certain degree because the heat is diffused from the exterior member; however, this may involve a problem of an increase in temperature of the exterior member of the distal end part of the ultrasonic endoscope and an increase in temperature in the periphery of the distal end part.

Also, with the ultrasonic endoscope or the like disclosed in JP2009-240755A, a high-frequency treatment tool is used, and hence a distal end main body case (exterior body) uses an electrically insulating resin. To allow washing, disinfection, and sterilization of the endoscope, the distal end main body case is required to be chemical resistant, and typically uses polysulfone, polyphenylsulfone, or polyetherimide. Owing to this, the distal end main body case has low thermal conductivity, and even through a member with high thermal conductivity is bonded to the electrically insulating resin, heat is not efficiently released.

Also, with the technologies disclosed in JP2009-240755A and JP2008-22077A, since heat is finally released by diffusing the heat to the exterior body, the surface temperature of the exterior body may rise, like the technology disclosed in JP5329065B.

Note that, since the technology disclosed in JP2008-22077A is used for a body surface of a subject, even when heat is diffused and released to the exterior body, the heat can be efficiently released to the outside of the body. However, if the technology disclosed in JP2008-22077A is applied to the ultrasonic endoscope that is used in a body cavity of a subject, this may increase the surface temperature of the exterior body. Therefore, it is difficult to satisfy the demand that the surface temperature of the insertion section is set to the predetermined temperature or lower.

Presently, in order to improve diagnostic accuracy of an ultrasonic endoscope, the transmission output of ultrasonic waves is increased by laminating ultrasonic transducers (vibrators), and reception sensitivity is increased by increasing the number of ultrasonic vibrators.

As the result, the amount of heat released from the ultrasonic vibrators is increased, and due to the heat generated from the ultrasonic vibrators, the temperature of the insertion section that contacts a body cavity wall, in particular, the temperature of the distal end part at which the ultrasonic vibrators are disposed may be increased.

Further, with the ultrasonic endoscope, to improve diagnostic accuracy by improving image quality or the like of an ultrasound image to be obtained, the driving voltage for driving the ultrasonic vibrators may be increased, in addition to increasing the reception sensitivity.

However, with such an ultrasonic endoscope, the heat generated from the ultrasonic vibrators (ultrasonic transducers) due to the increase in the driving voltage may cause a further temperature rise.

As described above, to improve the diagnostic accuracy by improving the image quality or the like of the ultrasound image, when the number of the ultrasonic vibrators is increased, when the driving voltage of the ultrasonic vibrators is increased, or when the transmission output of ultrasonic waves is increased, the technologies disclosed in JP5329065B, JP2009-240755A, and JP2008-22077A involve problems. The problems are possibly increasing the ambient temperatures, such as the ambient temperature of the distal end part of the ultrasonic endoscope that directly contacts the inside of a living body such as a human body, and the ambient temperature of the exterior member, to allowable temperatures or higher.

It is required to suppress heat generation and a temperature rise while the diameter of the insertion section and the size of the distal end part are held small, and a significant issue is how the heat generated from the ultrasonic vibrators is released.

Here, a metal endoscopic structure in an ultrasonic endoscope has large thermal capacity and high thermal conductivity, and hence by releasing the heat generated from ultrasonic vibrators to the metal endoscopic structure via a thermally conductive member such as a copper foil, the heat can be released to the proximal end side of the endoscope. However, since a voltage in a range from 10 V to 100 V is applied to the driving signal for driving the ultrasonic vibrators, the ultrasonic vibrator structure including the copper foil is required to be electrically insulated from the endoscopic structure. Thus, it is difficult to release the heat transmitted to the copper foil with high thermal conductivity, to the endoscopic structure.

The present invention addresses the above-described problems of related art, and it is an object of the present invention to provide an ultrasonic endoscope having a heat release structure that transmits the heat generated from ultrasonic vibrators to, for example, an electrically conductive endoscopic structure which is housed in a distal end part and which can efficiently release the heat, while the diameter of an insertion section is held small, the size of the distal end part is held small, and electric safety is secured. Further, it is an object of the present invention to provide an ultrasonic endoscope that can prevent a burn of an alimentary canal by suppressing a temperature rise of surface of the ultrasonic vibrators, and as a result, that can improve diagnostic accuracy in ultrasonic diagnosis.

To attain the above-described objects, an ultrasonic endoscope according to a first aspect of the present invention including a plurality of ultrasonic vibrators at a distal end part of the ultrasonic endoscope includes an ultrasonic vibrator unit provided at the distal end part, the ultrasonic vibrator unit being composed of at least an ultrasonic vibrator array and a first thermally conductive member, the ultrasonic vibrator array having the plurality of ultrasonic vibrators that are arranged in a cylindrical form, the first thermally conductive member being disposed thermally in contact with the ultrasonic vibrator array; a plurality of cables that are electrically connected to the ultrasonic vibrator array; and an electrically conductive structural body that is disposed to extend from a distal end side toward a proximal end side of the ultrasonic endoscope. The ultrasonic vibrator unit and the electrically conductive structural body are connected to each other via an electrically insulating second thermally conductive member.

In this case, the first thermally conductive member is preferably a cylindrical electrically conductive member that is in contact with the ultrasonic vibrator array.

Preferably, the electrically conductive structural body is a distal-end-side ring component of an angle assembly.

Preferably, the electrically conductive structural body is an integrated ground in which shields of the plurality of cables are connected to one another, and is connected to the first thermally conductive member via the second thermally conductive member.

Preferably, the second thermally conductive member is removably connected to the first thermally conductive member or the electrically conductive structural body.

Preferably, the second thermally conductive member has a withstand voltage of 1.5 kV or higher.

Preferably, the second thermally conductive member has a thickness of 3 mm or smaller.

Preferably, the second thermally conductive member has a thermal conductivity of 0.5 W/mK or higher.

Preferably, the second thermally conductive member is a ceramic member, a heat release sheet, a heat release pad, or an electrically insulating coating.

Preferably, the second thermally conductive member is a ceramic screw.

To attain the above-described objects, an ultrasonic endoscope according to a second aspect of the present invention including a plurality of ultrasonic vibrators at a distal end part of the ultrasonic endoscope includes an ultrasonic vibrator unit provided at the distal end part, the ultrasonic vibrator unit being composed of at least an ultrasonic vibrator array and a thermally conductive member, the ultrasonic vibrator array having the plurality of ultrasonic vibrators that are arranged in a cylindrical form, the thermally conductive member being disposed thermally in contact with the ultrasonic vibrator array; a plurality of cables that are electrically connected to the ultrasonic vibrator array; and an electrically conductive structural body that is disposed to extend from a distal end side toward a proximal end side of the ultrasonic endoscope. The ultrasonic vibrator unit and the electrically conductive structural body are connected to each other via the thermally conductive member.

Preferably, the electrically conductive structural body is an integrated ground in which shields of the plurality of cables are connected to one another, and is connected to the ultrasonic vibrator array via the thermally conductive member.

Preferably, the distal end part has a forceps lead-out port, and the forceps lead-out port is disposed on a distal end side with respect to the plurality of ultrasonic vibrators.

Preferably, in any of the first and second aspects, the plurality of ultrasonic vibrators are radial type.

With the present invention, the ultrasonic endoscope can be provided that has a heat release structure that transmits the heat generated from the ultrasonic vibrators to, for example, the electrically conductive endoscopic structure which is housed in the distal end part and which can efficiently release the heat from the electrically conductive endoscopic structure, while the diameter of the insertion section is held small, the size of the distal end part is held small, and electric safety is secured; that can prevent a burn of an alimentary canal by suppressing a temperature rise of surfaces of the ultrasonic vibrators; and as a result, that can improve diagnostic accuracy in ultrasonic diagnosis.

DESCRIPTION OF THE PREFERRED EMBODIMENTS

An ultrasonic endoscope according to the present invention is described below in detail based on preferred embodiments shown in the accompanying drawings.

First Embodiment

Figure 1:
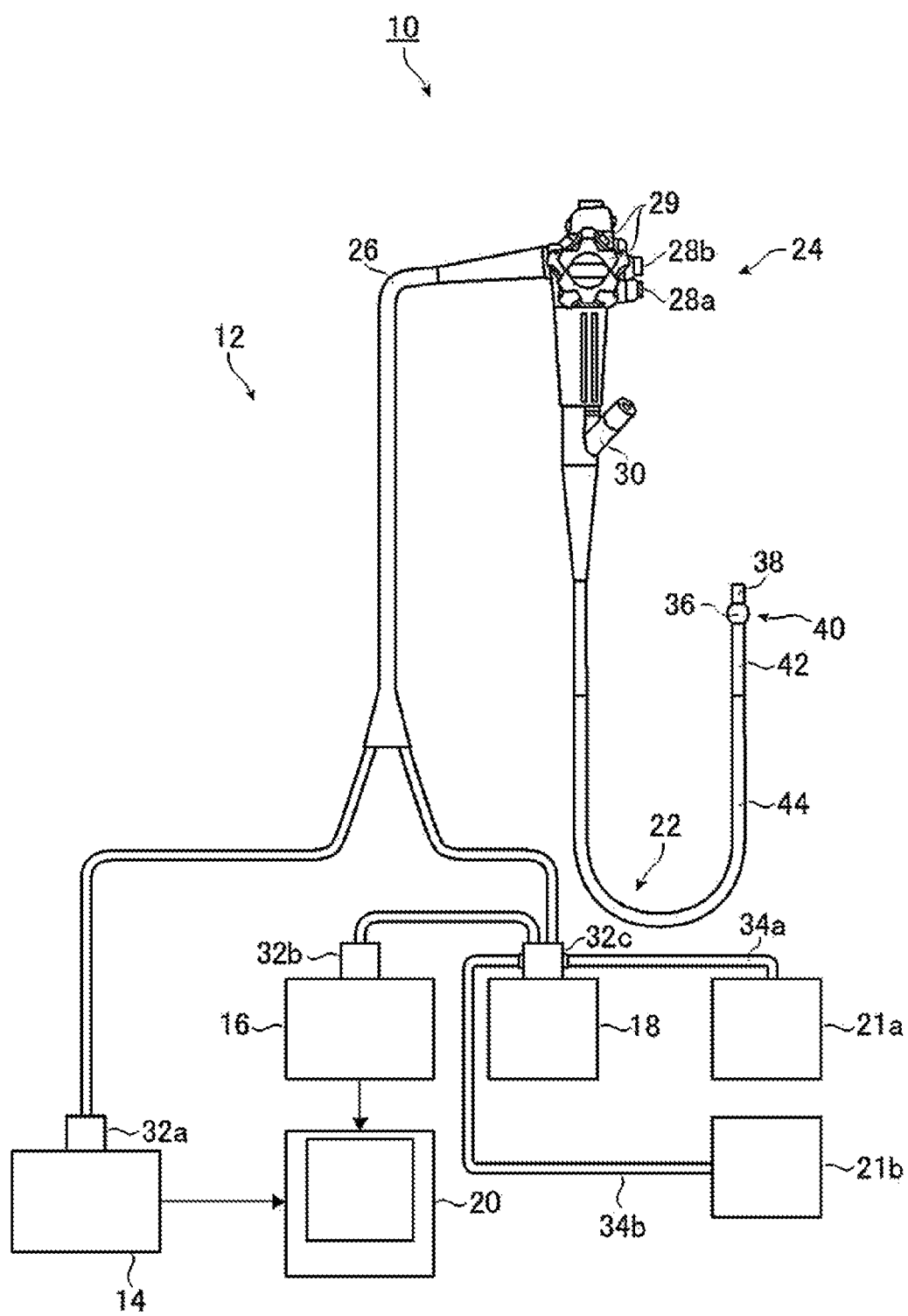
FIG. 1 is a schematic configuration diagram showing an example of a configuration of an ultrasonic inspection system that uses an ultrasonic endoscope according to an embodiment of the present invention.
Figure 2:
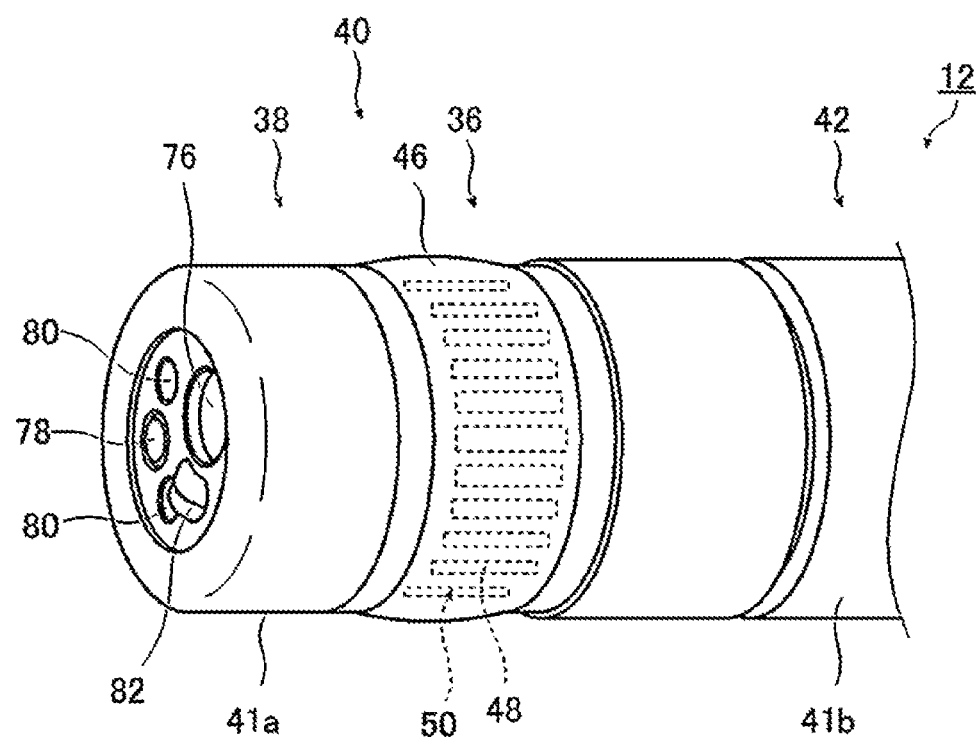
FIG. 2 is a partly enlarged perspective view showing an external appearance of an example of a distal end part of the ultrasonic endoscope shown in FIG. 1.
Figure 3:
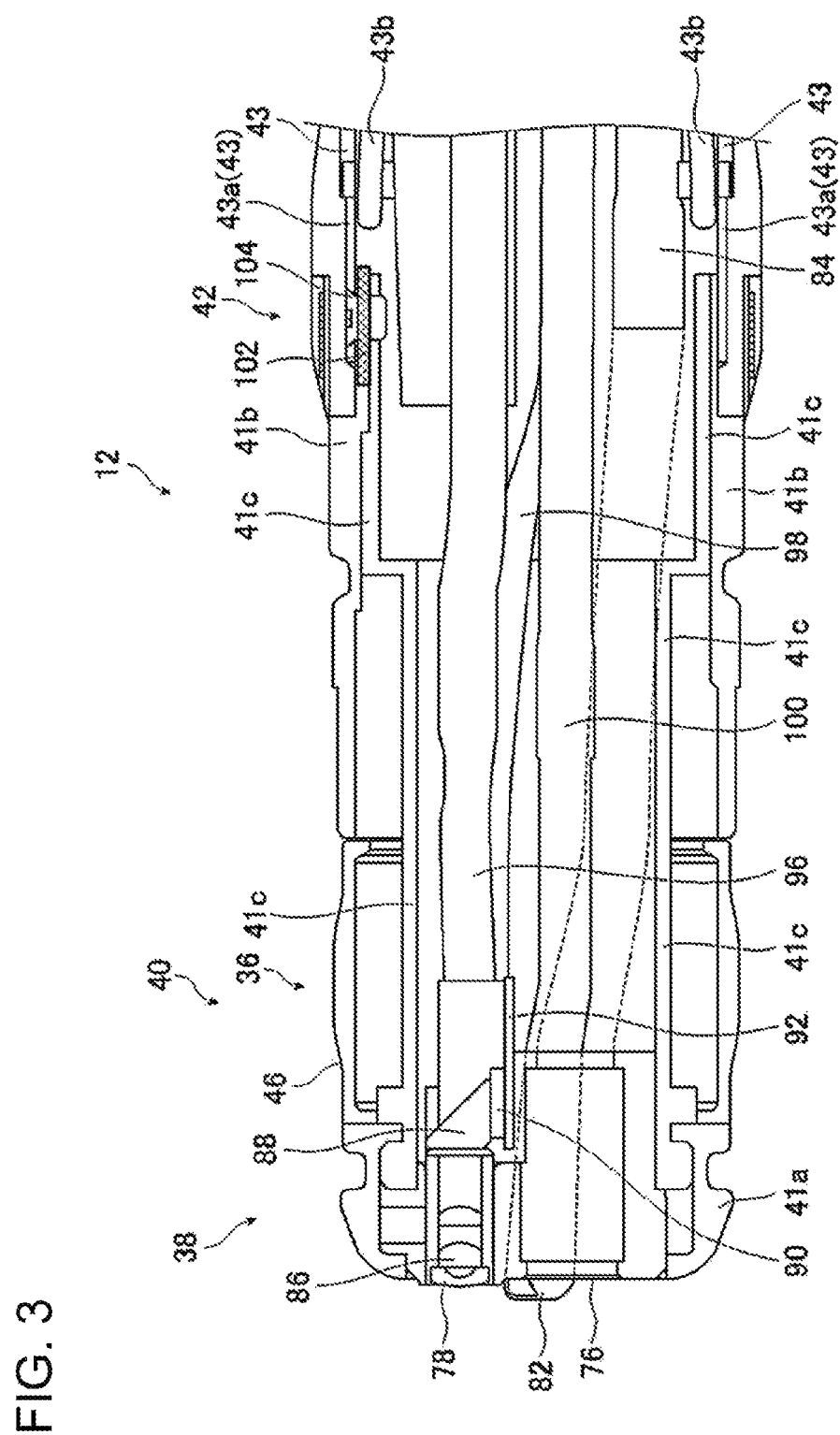
FIG. 3 is a longitudinal section of the distal end part of the ultrasonic endoscope shown in FIG. 2.
Figure 4:
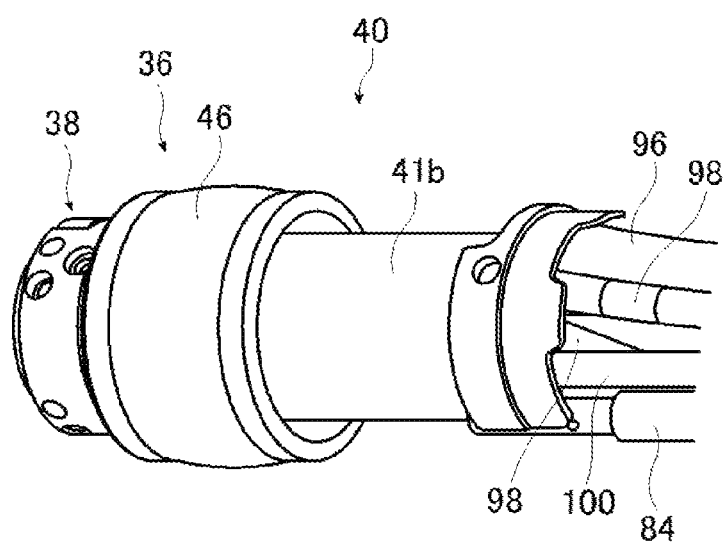
FIG. 4 is a partly exploded perspective view showing the distal end part of the ultrasonic endoscope shown in FIG. 2.
Figure 5:
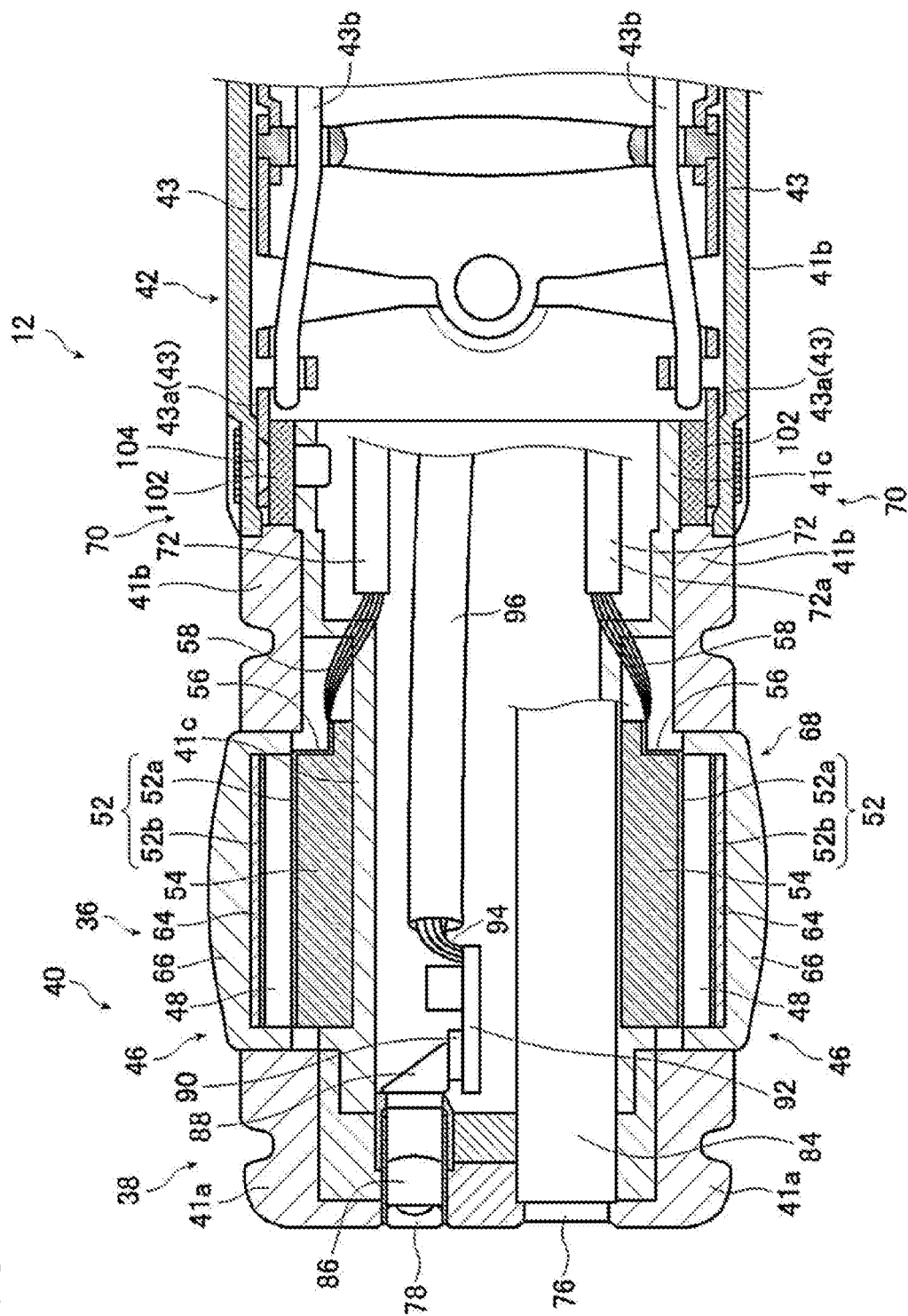
FIG. 5 is a longitudinal section schematically showing an example of a heat release structure of the distal end part of the ultrasonic endoscope shown in FIG. 3.

FIG. 1 is a schematic configuration diagram showing an example of a configuration of an ultrasonic inspection system that uses an ultrasonic endoscope according to an embodiment of the present invention. FIG. 2 is a partly enlarged perspective view showing an external appearance of an example of a distal end part of the ultrasonic endoscope shown in FIG. 1. FIG. 3 is a longitudinal section of the distal end part of the ultrasonic endoscope shown in FIG. 2. FIG. 4 is a partly exploded perspective view showing the distal end part of the ultrasonic endoscope shown in FIG. 2. FIG. 5 is a longitudinal section schematically showing a heat release structure of the distal end part of the ultrasonic endoscope shown in FIG. 3. Note that FIG. 5 emphasizes members relating to the heat release structure and so forth to explain the heat release structure of the ultrasonic endoscope of this embodiment. Hence, FIG. 5 is a drawing that emphasizes the part required for the explanation, whereas simplifies or omits the part not used for the explanation.

An ultrasonic inspection system 10 shown in FIG. 1 enables the gallbladder or the pancreas, which is difficult to be observed by an ultrasonic inspection from a body surface of a subject such as a patient, to be observed through an alimentary canal, such as the esophagus, stomach, duodenum, small intestine, large intestine, or the like, which is a body cavity of the subject. The ultrasonic inspection system 10 includes a plurality of ultrasonic vibrators arranged in a cylindrical form, and inserts an ultrasonic endoscope according to the present invention including an ultrasonic observation portion and an endoscopic observation portion into a body cavity of a subject. Note that the ultrasonic observation portion acquires an ultrasonic tomographic image. The endoscopic observation portion acquires an endoscope optical image. The ultrasonic tomographic image is hereinafter referred to as an ultrasound image, and the endoscope optical image is hereinafter referred to as an endoscope image. With this configuration, the ultrasonic inspection system 10 acquires an ultrasound image of an observation target region of a subject while observing an endoscope image of the subject.

Also, in the ultrasonic endoscope of the present invention, a first thermally conductive member is disposed. The first thermally conductive member is provided such that a radial-type ultrasonic vibrator unit including a plurality of ultrasonic vibrators that generate heat during an ultrasonic inspection takes a role of a heat release effect. The first thermally conductive member is, for example, a metal ring on which the ultrasonic vibrator unit is mounted and which supports the ultrasonic vibrator unit. Additionally/alternatively, in the ultrasonic endoscope of the present invention, an electrically/thermally conductive member, such as a thin sheet metal of a copper foil or the like that gives roles of a shield and a heat release effect to side surfaces of the plurality of ultrasonic vibrators or a ground is disposed. With this configuration, the ultrasonic endoscope of the present invention efficiently releases the heat while insulation of the heat transmitted from the ultrasonic vibrators to the electrically/thermally conductive member is secured, an increase in heat of the surfaces of the ultrasonic vibrators is suppressed, and hence a thermal burn of an alimentary canal can be prevented from occurring. In this case, the first thermally conductive member is, for example, the ultrasonic vibrator unit.

Hence, according to the present invention, the first thermally conductive member is disposed at a position as close as possible to an electrically/thermally conductive structural body disposed in an exterior member of a distal end body. With this configuration, the heat is transmitted from the plurality of ultrasonic vibrators to the electrically conductive structural body of the ultrasonic endoscope via the electrically/thermally conductive member, and is released from the structural body. At this time, according to the present invention, to further secure electric safety, a second thermally conductive member having electrically insulating properties is disposed between the electrically conductive structural body and the electrically conductive first thermally conductive member, and a thermally conductive electrically insulating layer is provided between the first thermally conductive member and the electrically conductive structural body. With this configuration, according to the present invention, the heat is transmitted to the electrically conductive structural body of the ultrasonic endoscope while electric insulation properties are secured.

The first thermally conductive member is, for example, an electrically/thermally conductive member such as a metal ring, and/or a copper foil, or an electrically/thermally conductive member connected to a copper foil. The electrically/thermally conductive structural body is, for example, a metal endoscope structure such as a distal-end-side ring component of an angle assembly, or an integrated ground of a plurality of cables of a shield cable connected to the plurality of ultrasonic vibrators.

As shown in FIG. 1, the ultrasonic inspection system 10 includes an ultrasonic endoscope 12 according to a first embodiment of the present invention having a heat release structure at a distal end part thereof, an ultrasonic processor device 14 that generates an ultrasound image, an endoscopic processor device 16 that generates an endoscope image, a light source device 18 that supplies illumination light that illuminates a body cavity to the ultrasonic endoscope 12, and a monitor 20 that displays the ultrasound image and/or the endo scope image.

The ultrasonic inspection system 10 further includes a water supply tank 21a that stores washing water or the like, and a suction pump 21b that sucks an object to be sucked in the body cavity. Although not shown, the ultrasonic inspection system 10 may further include a supply pump or the like that supplies washing water in the water supply tank 21a or gas such as the outside air to a pipe line (not shown) in the ultrasonic endoscope 12.

First, as shown in FIGS. 1 to 5, the ultrasonic endoscope 12 according to the present invention has an ultrasonic observation portion 36 including a heat release structure 70 being a feature of the present invention, and an endoscopic observation portion 38 at a distal end part 40, image captures the inside of a body cavity of a subject, and acquires an ultrasound image (echo signal) and an endoscope image (image signal).

The ultrasonic endoscope 12 is composed of an insertion section 22 that includes the endoscopic observation portion 38 and the ultrasonic observation portion 36 at the distal end part, and that is inserted into the body cavity of the subject; an operation section 24 that is connected to a proximal end part of the insertion section 22 and with which an operator, such as a doctor or a technician, performs an operation; and a universal cord 26 having one end connected to the operation section 24.

In the operation section 24, an air/water supply button 28a that opens and closes an air/water supply pipe line (not shown) from the water supply tank 21a, and a suction button 28b that opens and closes a suction pipe line (not shown) from the suction pump 21b are disposed side by side; and a pair of angle knobs 29, 29, and a treatment tool insertion port (forceps port) 30 are provided.

In this case, the water supply tank 21a is for storing washing water or the like that is supplied to the air/water supply pipe line in the ultrasonic endoscope 12 for washing the endoscopic observation portion 38 and so forth of the ultrasonic endoscope 12. Note that the air/water supply button 28a is used for ejecting gas such as the air and water such as the washing water that are supplied through the air/water supply pipe line from the water supply tank 21a, from the endoscopic observation portion 38 on the distal end side of the insertion section 22.

The suction pump 21b sucks the suction pipe line (not shown) for sucking the object to be sucked in the body cavity from the distal end side of the ultrasonic endoscope 12. Note that the object to be sucked in the above situation includes the supplied washing water. The suction button 28*b* is used for sucking the object to be sucked in the body cavity from the distal end side of the insertion section 22 with the sucking force by the suction pump 21*b*.

Also, the treatment tool insertion port 30 allows a treatment tool, such as forceps, a puncture needle, or a surgical knife, to be inserted therethrough.

The other end part of the universal cord 26 is provided with an ultrasonic connector 32*a* that is connected to the ultrasonic processor device 14, an endoscope connector 32*b* that is connected to the endoscopic processor device 16, and a light source connector 32*c* that is connected to the light source device 18. The ultrasonic endoscope 12 is removably connected to the ultrasonic processor device 14, the endoscopic processor device 16, and the light source device 18 respectively through the connectors 32*a*, 32*b*, and 32*c*. The light source connector 32*c* is also connected to an air/water supply tube 34*a* for connection with the water supply tank 21*a*, and a suction tube 34*b* for connection with the suction pump 21*b*.

The insertion section 22 is composed of, in order from the distal end side, the distal end part (distal end rigid part) 40 that is formed of a rigid member and has the ultrasonic observation portion 36 and the endoscopic observation portion 38; a bending part 42 that is connected to the proximal end side of the distal end part 40, that is formed of a plurality of bending pieces (angle rings) coupled to one another, and that is bendable; and a soft part 44 that couples the proximal end side of the bending part 42 with the distal end side of the operation section 24, and that is thin, long, and flexible.

As shown in FIG. 5, the bending part 42 consists of an angle assembly having an angle ring structure in which a plurality of angle rings (nodal rings) 43 each of which is a ring part formed in a ring-like shape are pivotally connected to one another in an axial direction. A plurality of operating wires 43*b* are disposed in the angle rings 43 at a predetermined interval in the axial direction of inner peripheral surfaces of the angle rings 43. The proximal ends of the operating wires 43*b* are connected to a pulley (not shown) that is rotated by the pair of angle knobs 29, 29 provided at the operation section 24. Thus, when the pair of angle knobs 29, 29 are rotationally operated and the pulley is rotated, the operating wires are pulled and the bending part 42 bends in a desirable direction. By operating the pair of angle knobs 29, 29 as described above, the bending part 42 is remotely operated to bend and the distal end part 40 can be headed in a desirable direction.

In addition, a balloon into which an ultrasound conveyance medium (for example, water or oil) that covers the ultrasonic observation portion 36 is injected may be removably attached to the inside of the distal end part 40. Since ultrasonic waves and echo signals are markedly attenuated in the air, the balloon is inflated by injecting the ultrasound conveyance medium into the balloon, and the inflated balloon is brought into contact with an observation target region. Thus, the air is eliminated from the area between an ultrasonic vibrator array 50 of the ultrasonic observation portion 36 and the observation target region, and the attenuation in ultrasonic waves and echo signals can be prevented.

The ultrasonic processor device 14 generates and supplies an ultrasonic signal (data) for causing the ultrasonic vibrator array 50 of the ultrasonic observation portion 36 of the distal end part 40 of the insertion section 22 of the ultrasonic endoscope 12 to generate ultrasonic waves. An echo signal (data) is reflected from the observation target region on which ultrasonic waves have been emitted. The ultrasonic processor device 14 receives the echo signal by using the ultrasonic vibrator array 50. Furthermore, the ultrasonic processor device 14 generates an ultrasound image that is displayed on the monitor 20 by performing various signal (data) processing on the acquired echo signal.

With the endoscopic processor device 16, the endoscopic observation portion 38 of the distal end part 40 of the insertion section 22 of the ultrasonic endoscope 12 receives and acquires a image signal (data) acquired from the observation target region illuminated with the illumination light from the light source device 18. Furthermore, the endoscopic processor device 16 generates an endoscope image that is displayed on the monitor 20 by performing various signal (data) processing and image processing on the acquired image signal.

The processor devices 14 and 16 may be composed of a processor of, for example, a personal computer (PC).

To image capture the observation target region in the body cavity by the endoscopic observation portion 38 of the ultrasonic endoscope 12 and to acquire an image signal, the light source device 18 generates illumination light, such as white light that consists of three primary colors of light of red light (R), green light (G), and blue light (B), or specific wavelength light. The light source device 18 supplies the generated illumination light to the ultrasonic endoscope 12, and the illumination light propagates on a light guide (not shown) or the like in the ultrasonic endoscope 12. Furthermore, the light source device 18 emits the propagating light from the endoscopic observation portion 38 of the distal end part 40 of the insertion section 22 of the ultrasonic endoscope 12, and illuminates the observation target region in the body cavity.

The monitor 20 receives respective image signals generated by the ultrasonic processor device 14 and the endoscopic processor device 16, and displays an ultrasound image and an endoscope image. When the ultrasound image and the endoscope image are to be displayed, only one of the images may be selectively displayed, or both the images may be simultaneously displayed on the monitor 20. A monitor for displaying an ultrasound image and a monitor for displaying an endoscope image may be individually provided. Alternatively, an ultrasound image and an endoscope image may be displayed in any other desirable form.

The configurations of the distal end part and the bending part of the insertion section of the ultrasonic endoscope are described below in detail with reference to FIGS. 2 to 5.

As shown in FIGS. 2 to 5, the distal end part 40 of the ultrasonic endoscope 12 is provided with the ultrasonic observation portion 36 for acquiring an ultrasound image on the proximal end side, and the endoscopic observation portion 38 for acquiring an endoscope image on the distal end side.

The distal end part 40 of the ultrasonic endoscope 12 includes a cap-shaped distal end component 41*a* that caps the distal end of an endoscope component of the endoscopic observation portion 38 at the distal end; a proximal-end-side ring 41*b* disposed on the proximal end side of the ultrasonic observation portion 36 on the proximal end side; and a metal ring 41*c* made of, for example, SUS that connects and fixes the distal end component 41*a* and the proximal-end-side ring 41*b*. The distal end component 41*a* and the proximal-end-side ring 41*b* are made of a rigid member such as a hard resin, and are exterior members.

An endoscope component of the endoscopic observation portion 38 is disposed at a distal end portion of a ring inner portion on the inner side of the metal ring 41*c*. Various members, such as a pipe line extending from the endoscope component toward the proximal end side and a transmission path, are stored in the ring inner portion (in the inner periphery) connected to the endoscope component. Also, the cylindrical ultrasonic vibrator array 50 of the ultrasonic observation portion 36 is wound around and integrated with an outer portion (outer periphery) of the metal ring 41c on the distal end side of the endoscopic observation portion 38, thereby constituting a vibrator unit 46. The metal ring 41c may be composed of two cylindrical members including a cylindrical member having a portion that is partly cut out in view of convenience for processing and assembly. Since the combination of the two cylindrical members of the metal ring 41c provides one function, the present invention handles the combination of the two cylindrical members as one component.

As it is clear from the above description, the distal end part 40 of the ultrasonic endoscope 12 can be disassembled into the ultrasonic vibrator unit 46 including the distal end component 41a, the proximal-end-side ring 41b, and the metal ring 41c.

The endoscopic observation portion 38 includes a treatment tool lead-out port 76, an observation window 78, an illumination window 80, and a washing (air/water supply) nozzle 82 provided in a distal end surface of the endoscopic observation portion 38.

The treatment tool lead-out port 76 is an exit of a treatment tool channel 84 that extends toward the proximal end side and communicates with the treatment tool insertion port 30 of the operation section 24. A treatment tool such as forceps that are inserted into the treatment tool channel 84 from the treatment tool insertion port 30 of the operation section 24 protrudes from the treatment tool lead-out port 76, and treatment is performed on a subject.

Note that the treatment tool lead-out port is so-called forceps lead-out port. Also, the treatment tool insertion port is so-called forceps port. Further, the treatment tool channel is so-called forceps pipe line.

In the example shown in FIGS. 2 to 5, the treatment tool lead-out port 76 is provided at the endoscopic observation portion 38 at the distal end of the distal end part 40. However, the present invention is not particularly limited to the illustrated example. The treatment tool lead-out port 76 may be provided at any location as far as the location is on the distal end side of the ultrasonic endoscope 12 with respect to the plurality of ultrasonic vibrators 48 of the ultrasonic observation portion 36.

That is, the ultrasonic endoscope to which the heat release structure according to the present invention is applied has to be an ultrasonic endoscope having a treatment tool lead-out port disposed on the distal end side with respect to the ultrasonic vibrators.

An objective lens 86, a prism 88, and a solid-state imaging element 90 are disposed on the rear side (proximal end side) of the observation window 78. The reflected light of the observation target region incident through the observation window 78 is taken in with the objective lens 86. The optical path of the taken-in reflected light is folded at right angle by the prism 88, and the reflected light forms an image on an imaging surface of the solid-state imaging element 90. The solid-state imaging element 90 photoelectrically converts the reflected light of the observation target region, the reflected light which has been transmitted through the observation window 78, the objective lens 86, and the prism 88 and has formed an image on the imaging surface, into an image signal and outputs the image signal. The solid-state imaging element may be a charge coupled device (CCD), complementary metal oxide semiconductor (CMOS), or the like.

The solid-state imaging element 90 is mounted on a substrate 92. The substrate 92 has formed thereon a circuit pattern that is electrically connected to the solid-state imaging element 90. The circuit pattern has electrodes that are connected to a plurality of wiring cables 94. The wiring cables 94 are composed of wirings coated with electrically insulating tubes. The circuit pattern of the substrate 92 transmits a signal of an endoscope image which is an optical image, and hence the circuit pattern of the substrate 92 and the wiring cables 94 serve as an imaging element signal transmission path. The plurality of wiring cables 94 extend toward the bending part 42, are inserted through the universal cord 26 from the operation section 24, and are finally connected to the endoscope connector 32b. The endoscope connector 32b is connected to the endoscopic processor device 16. The plurality of wiring cables 94 are preferably covered with a shield member and provided as a shield cable 96.

The image signal output from the solid-state imaging element 90 is transmitted to the endoscopic processor device 16 through the universal cord 26 via the wiring cables 94 extending from the insertion section 22 to the operation section 24. The endoscopic processor device 16 performs various signal processing and image processing on the transmitted image signal, and displays the processed image signal as an endoscope optical image on the monitor 20.

The illumination window 80 includes two illumination windows 80 provided with the observation window 78 interposed therebetween. The illumination windows 80 are connected to the emission end of a light guide 98 (see FIG. 3). The light guide 98 extends from the insertion section 22 to the operation section 24. The incident end of the light guide 98 is connected to the light source device 18 connected through the universal cord 26. That is, the light guide 98 extends toward the bending part 42, is inserted through the universal cord 26 from the operation section 24, and is finally connected to the light source connector 32c. The light source connector 32c is connected to the light source device 18. The illumination light emitted from the light source device 18 propagates through the light guide 98, and is emitted on an observation target region through the illumination windows 80.

The washing nozzle 82 is connected to an air/water supply channel (pipe line) 100. The air/water supply channel 100 extends toward the bending part 42, and is inserted through the universal cord 26 from the operation section 24. Further, the air/water supply channel 100 is connected to the light source connector 32c, and is connected to the water supply tank 21a via the air/water supply tube 34a. The washing nozzle 82 ejects the air or washing water from the water supply tank 21a via the air/water supply channel 100 in the ultrasonic endoscope 12, to the observation window 78 and the illumination windows 80 for washing the observation window 78 and the illumination windows 80.

The ultrasonic observation portion 36 is described next with reference to FIG. 5.

As shown in FIG. 5, the ultrasonic vibrator unit 46 that constitutes the ultrasonic observation portion 36 has the ultrasonic vibrator array 50 in which the plurality of ultrasonic vibrators (transducers) 48 are arranged in a cylindrical form; an electrode part 52 including a plurality of individual electrodes 52a corresponding to the plurality of ultrasonic vibrators 48, and a common electrode 52b common to the plurality of ultrasonic vibrators 48; a flexible printed circuit (FPC) 56 connected to the plurality of individual electrodes 52a; and the metal ring 41c that supports the ultrasonic vibrator array 50 wound around the outer periphery thereof.

The ultrasonic vibrator unit 46 further has an acoustic matching layer 64 laminated on the ultrasonic vibrator array 50, and an acoustic lens 66 laminated on the acoustic matching later 64. That is, the ultrasonic vibrator unit 46 consists of a laminated body 68 of the acoustic lens 66, the acoustic matching later 64, the ultrasonic vibrator array 50, and a backing material layer 54. It can be said that the laminated body 68 is coupled with the metal ring 41c by a method of fitting or the like and hence is integrated with the metal ring 41c.

The acoustic matching layer 64 is provided on the outer periphery of the ultrasonic vibrator array 50, for acoustic impedance matching between a subject such as a human body and the ultrasonic vibrators 48.

The acoustic lens 66 attached to the outer periphery of the acoustic matching layer 64 is for converging the ultrasonic waves emitted from the ultrasonic vibrator array 50 toward the object target portion. The acoustic lens 66 consists of, for example, a silicone-based resin (millable-based silicone rubber (HTV rubber), liquid silicone rubber (RTV rubber), or the like), a butadiene-based resin, a polyurethane-based resin, or the like. To secure the acoustic impedance matching between the subject and the ultrasonic vibrators 48 by the acoustic matching layer 64, and hence to increase transmittance of ultrasonic waves, the acoustic lens 66 has mixed therein powder of, for example, titanium oxide, alumina, or silica if required.

The ultrasonic vibrator array 50 is an array of a plurality of channels, for example, 48 to 192 channels (CH) consisting of a plurality of, for example, 48 to 192 rectangular-parallelepiped ultrasonic vibrators (transducers) 48 which are arranged in a cylindrical form.

That is, the ultrasonic vibrator array 50 consists of the plurality of ultrasonic vibrators 48 arranged in, for example, a cylindrical two-dimensional array at a predetermined pitch, like the illustrated example. The ultrasonic vibrators 48 that constitute the ultrasonic vibrator array 50 are arranged at an equivalent interval in a cylindrical form around the axial direction of the distal end part 40 (longitudinal axial direction of the insertion section 22) as described above. Further, the ultrasonic vibrators 48 are successively driven on the basis of the driving signal input from the ultrasonic processor device 14. Thus, radial electronic scanning is performed in a range in which the ultrasonic vibrators 48 are arranged, as a scanning range.

The ultrasonic vibrator array 50 is disposed on the outer peripheral surface of the cylindrical backing material layer 54. The ultrasonic vibrators 48 have a configuration in which electrodes are formed on a bottom surface of a piezoelectric thick film of, for example, lead zirconate titanate (PZT) or polyvinylidene fluoride (PVDF). One of the electrodes is the individual electrode 52a individually and independently provided for each of the ultrasonic vibrators 48, and the other electrode is the common electrode (for example, ground electrode) 52b common to all the ultrasonic vibrators 48.

Although not shown, the gap between two adjacent ultrasonic vibrators 48 is filled with a filling material such as an epoxy resin.

With the ultrasonic vibrator unit 46 of the ultrasonic observation portion 36, the respective ultrasonic vibrators 48 of the ultrasonic vibrator array 50 are driven, and a voltage is applied to both the electrodes 52a and 52b of the ultrasonic vibrators 48. When the voltage is applied, the piezoelectric bodies vibrate and successively generate ultrasonic waves, and emit the ultrasonic waves toward the observation target region of the subject. The plurality of ultrasonic vibrators 48 are successively driven using an electronic switch such as a multiplexer, and hence radial scanning is performed with the ultrasonic waves in a scanning range along a cylindrical surface on which the ultrasonic vibrator array 50 is disposed, or for example, in a range by several tens of millimeters from the center of the cylindrical surface.

Consequently, each of the ultrasonic vibrators 48 of the ultrasonic vibrator array 50 generates heat when generates ultrasonic waves, and further the backing material layer 54 generates heat due to an effect of the ultrasonic waves.

Also, when the ultrasonic vibrator array 50 receives the echo signal (ultrasonic echo) reflected from the observation target region, the piezoelectric body vibrates and generates a voltage. The ultrasonic vibrator array 50 outputs the voltage, as an electric signal (ultrasound detection signal) corresponding to the received ultrasonic echo, to the ultrasonic processor device 14. The electric signal is subjected to various signal processing by the ultrasonic processor device 14, and then displayed as an ultrasound image on the monitor 20.

As shown in FIG. 5, the electrode part 52 is provided on an outer surface or an inner surface of the ultrasonic vibrator array 50, along the central line of the cylindrical array, at the plurality of (48 to 192) ultrasonic vibrators 48 arranged in the cylindrical form of the cylindrical ultrasonic vibrator array 50.

The plurality of (48 to 192) individual electrodes 52a of the electrode part 52 having electric continuity individually with the plurality of (48 to 192) ultrasonic vibrators 48 are connected to the inner surfaces (inner peripheral surface side) of the plurality of ultrasonic vibrators 48 in the illustrated example. The common electrode 52b of the electrode part 52 common to the plurality of (48 to 192) ultrasonic vibrators 48 is connected to the outer surfaces (outer peripheral surface side) of the plurality of ultrasonic vibrators 48 in the illustrated example.

The plurality of individual electrodes 52a and the common electrode 52b of the electrode part 52 are preferably provided as electrode pads.

The backing material layer 54 supports the respective ultrasonic vibrators 48 of the ultrasonic vibrator array 50 from the lower surface side, that is, from the inner peripheral surface side.

The backing material layer 54 is a layer of a member that supports the plurality of ultrasonic vibrators 48 arranged in an array form. As shown in FIG. 5, the backing material layer 54 consists of a backing material located at the inner side (center side) of the plurality of ultrasonic vibrators 48 arranged in the cylindrical form. That is, the backing material layer 54 consists of the backing material disposed on the inner peripheral surface side (center side) of the ultrasonic vibrator array 50. The backing material layer 54 is also formed in a cylindrical shape.

The backing material that constitutes the backing material layer 54 functions as a cushion material that flexibly supports the respective ultrasonic vibrators 48 of the ultrasonic vibrator array 50. Hence, the backing material consists of a material having stiffness such as hard rubber, and an ultrasound attenuating material (ferrite, ceramic, etc.) is added to the material if required.

Thus, the ultrasonic vibrator array 50 is configured such that, in the illustrated example, the plurality of rectangular-parallelepiped ultrasonic vibrators 48 are arranged on the cylindrical outer surface (outer peripheral surface) of the cylindrical backing material layer 54, in such a way that the longitudinal direction of the ultrasonic vibrators 48 extends parallel to the center of the cylinder. Further preferably, the ultrasonic vibrator array 50 has an equidistant arrangement. That is, the plurality of ultrasonic vibrators 48 of the ultrasonic vibrator array 50 are arranged in a cylindrical form on the outer peripheral surface of the cylindrical backing material layer 54.

As shown in FIG. 5, the FPC 56 is attached to the side surface on the proximal end side of the backing material layer 54. The FPC 56 has a plurality of wiring patterns electrically connected to the plurality of individual electrodes 52*a* of the electrode part 52 on one side, whereas connects wiring of signal lines 58*a* of a plurality of coaxial cables 58 on the other side. A plurality of connection portions at one end portion of the FPC 56 are electrically connected to the plurality of individual electrodes 52*a* provided on the inner surface of the ultrasonic vibrator array 50. A plurality of connection portions at the other end portion of the FPC 56 are connected to the signal lines 58*a* of the plurality of coaxial cables 58 through wiring. In this way, the individual electrode 52*a* of each of the ultrasonic vibrators 48 of the ultrasonic vibrator array 50 is electrically connected to the signal line 58*a* of corresponding one of the coaxial cables 58.

Although not shown, the common electrode 52*b* of the electrode part 52 is connected to a ground bar or an integrated ground by wiring or the like. The ground bar or the integrated ground is preferably connected to shield members 58*c* of the plurality of coaxial cables 58.

Note that, in the present invention, the ground wiring or the like of the FPC 56 that is connected to the common electrode 52*b* of the electrode part 52 may be connected to the angle rings 43 and an endoscopic structure such as the integrated ground, and may be used for releasing heat.

However, for easy connection to the plurality of individual electrodes 52*a* of the electrode part 52, the FPC 56 is preferably composed of a circuit board, for example, a flexible printed circuit (hereinafter, merely referred to as FPC), a printed circuit board (hereinafter, PCB), or a printed wired board (hereinafter, PWB). Further, the FPC 56 preferably has a plurality of (48 to 192) wiring for electric connection with the plurality of (48 to 192) individual electrodes 52*a* of the electrode part 52, and a plurality of connection portions that are individually connected to the plurality of (48 to 192) wiring.

In this case, the FPC 56 may be composed of a single circuit board, for example, a flexible circuit board such as FPC; or a rigid circuit board, such as PCB or PWB. Further, the FPC 56 may be composed of a multilayer circuit board in which a flexible circuit board such as FPC; and a rigid circuit board, such as PCB or PWB, are integrated. For example, as the FPC 56, one in which FPC having a plurality of (48 to 192) wiring, and a rigid circuit board having a plurality of (48 to 192) connection portions are integrated such that the plurality of (48 to 192) wiring are individually connected to the plurality of (48 to 192) connection portions may be used. The plurality of (48 to 192) wiring are wiring for electric connection individually with the plurality of (48 to 192) individual electrodes 52*a* of the electrode part 52. Further, the plurality of (48 to 192) connection portions are connection portions for connecting wiring of the signal lines 58*a* of the plurality of coaxial cables 58 through wiring.

Thus, the plurality of wiring of the FPC 56 can be easily individually electrically connected to the plurality of individual electrodes 52*a* of the electrode part 52 of the ultrasonic vibrator array 50.

In this case, the electric connection between the plurality of wiring of the FPC 56 and the plurality of individual electrodes (electrode pads) 52*a* of the electrode part 52 of the ultrasonic vibrator array 50 may be provided by using an anisotropic electrically conductive sheet or anisotropic electrically conductive paste, or may be provided by heat seal. The electric connection is not limited to the above-described connection method, and may use any method as far as the connection method does not degrade workability of wiring and does not raise the degree of difficulty of working processes. Specifically, a known method, such as wire bonding or soldering, may be used.

Accordingly, an ultrasonic endoscope using an ultrasonic vibrator unit having a wiring structure can be provided in which the wiring work for the ultrasonic vibrators can be improved in simplification, efficiency, and workability; the ultrasonic vibrator array can be downsized; workability is good when the respective electrodes of the ultrasonic vibrator array are connected to the multiple cables through wiring; the level of difficulty of the working process is low; a load is less applied to the cables; and the risk of disconnection is low.

Thus, the wiring work for the ultrasonic vibrators can be improved in simplification, efficiency, and workability. Further, with the above-described configuration, the ultrasonic vibrator array can be downsized. Furthermore, with the above-described configuration, workability is good when the respective electrodes of the ultrasonic vibrator array are connected to the multiple cables through wiring, and the level of difficulty of the working process is low. Accordingly, an ultrasonic endoscope using an ultrasonic vibrator unit having a wiring structure can be provided in which a load is less applied to the cables, and the risk of disconnection is low.

Figure 6:
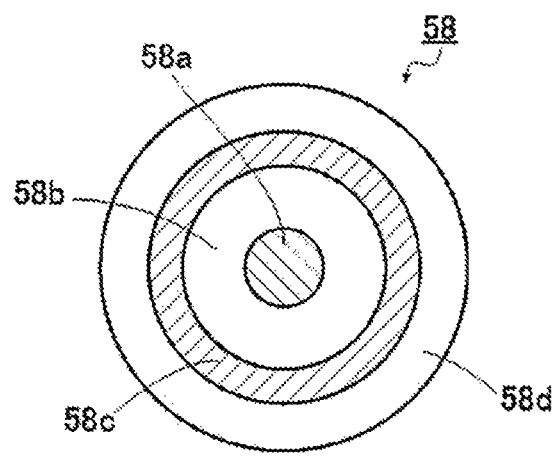
FIG. 6 is a cross section schematically showing a configuration of an example of a coaxial cable that is used for an ultrasonic observation portion of the distal end part of the ultrasonic endoscope shown in FIG. 5.

As shown in FIG. 6, the coaxial cable 58 used for the present invention includes a signal line 58*a* at the center, a first electrically insulating layer 58*b* on the outer periphery of the signal line 58*a*, a shield member 58*c* on the outer periphery of the first electrically insulating layer 58*b*, and a second electrically insulating layer 58*d* on the outer periphery of the shield member 58*c*. In other words, the coaxial cable 58 is configured such that the signal line 58*a*, the first electrically insulating layer 58*b*, the shield member 58*c*, and the second electrically insulating layer 58*d* are coaxially laminated from the center side.

Figure 7:
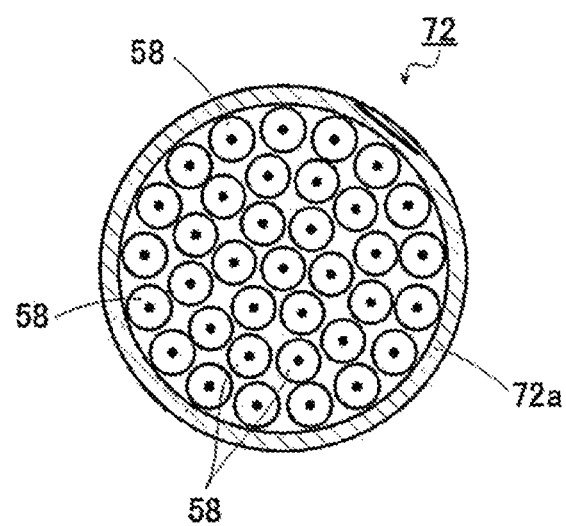
FIG. 7 is a cross section schematically showing an example of a shield cable composed of a plurality of coaxial cables that are used for the ultrasonic observation portion of the distal end part of the ultrasonic endoscope shown in FIG. 5.

In this case, according to the present invention, as shown in FIG. 7, the plurality of coaxial cables 58 are covered with an outer cover 72*a* at the outermost layer, and used as a single shield cable 72.

Note that the shield cable consisting of the plurality of ultrasonic cables used for the present invention is not limited to the shield cable 72 in which the plurality of coaxial cables 58 are covered with the outer cover 72*a*. For example, the shield cable may be a non-coaxial cable configured such that a plurality of signal lines each of which includes a central conductor and an electrically insulating layer of a dielectric or the like that covers the outer periphery of the central conductor, and a plurality of drain lines consisting of a conductor that functions as a shield member are disposed in a randomly mixed manner and serve as a single cable unit. Alternatively, the shield cable may be a non-coaxial cable configured such that a plurality of signal lines each of which includes a central conductor and an electrically insulating layer of a dielectric or the like that covers the outer periphery of the central conductor are disposed on the center side, a plurality of external conductors that function as a shield member are disposed around the plurality of signal lines, and the entirety is covered with a shielding material so as to serve as a single cable unit.

As described above, each of the shield members 58c of the plurality of coaxial cables 58 of the single shield cable 72 is electrically connected to a ground bar or the like to which the common electrode 52b of the electrode part 52 is connected.

Such a ground bar may be any ground bar as long as the plurality of shield members 58c of the plurality of coaxial cables 58 can be electrically connected to the ground bar by, for example, soldering, and as long as the ground bar is a known ground bar used for an ultrasonic endoscope.

For electric connection to the ground bar of the plurality of shield members 58c and for electric connection to the plurality of connection portions of the FPC 56 of the plurality of signal lines 58a, first, the outer cover 72a on the distal end side of the single shield cable 72 is stripped off and removed, and the plurality of coaxial cables 58 are taken out. Then, the second electrically insulating layers 58d on the distal end side of the plurality of taken-out coaxial cables 58 are stripped off and removed, and the plurality of shield members 58c are exposed to the outside. Finally, distal end portions of the plurality of shield members 58c exposed to the outside are cut and removed while proximal end sides of the shield members 58c remain without being removed, and distal end portions of the second electrically insulating layers 58d are stripped off and removed. Hence the plurality of signal lines 58a are exposed to the outside.

Thus, the plurality of shield members 58c remaining while being exposed to the outside of the plurality of coaxial cables 58 are electrically connected to the ground bar by soldering or other method.

Also, the plurality of signal lines 58a exposed to the outside at the distal ends of the plurality of coaxial cables 58 are individually electrically connected to the plurality of connection portions of the FPC 56 by soldering or other method.

Note that, instead of the ground bar, an integrated ground that binds the plurality of shield members 58c of the plurality of coaxial cables 58 and collectively connects the shield members 58c may be used, and the common electrode 52b of the electrode part 52 may be connected to the integrated ground via an electrically conductive member.

When the ultrasonic vibrator unit 46 is attached to the metal ring 41c of the distal end part 40 of the ultrasonic endoscope 12, a space for the connection portion between the FPC 56 attached to the side surface of the backing material layer 54 of the laminated body 68 of the ultrasonic vibrator unit 46 and the plurality of coaxial cables 58 (the signal lines 58a, the shield members 58c, and so forth), a gap between the plurality of coaxial cables 58, and a gap (space) through which the plurality of coaxial cables 58 pass are preferably filled with a filling material having high heat release effect, and the filling material preferably forms a filling material layer (not shown). The filling material that forms the filling material layer may use any filling material as long as the filling material is an electrically non-conductive filling material, such as an epoxy resin or a silicone-based filling material.

Such a filling material layer is provided to fill a gap between the FPC 56 of the ultrasonic vibrator unit 46 and the proximal-end-side ring 41b, and more particularly a gap between the plurality of coaxial cables 58 arranged at the FPC 56 and the proximal-end-side ring 41b. Further, the filling material layer fixes the FPC 56 to wiring portions and part of extension portions of the plurality of coaxial cables 58, and hence can prevent occurrence of faulty connection of the signal lines 58a of the coaxial cables 58 at the plurality of connection portions of the FPC 56, occurrence of faulty connection of the shield members 58c of the coaxial cables 58 at the ground bar or the like, and disconnection due to unbinding of the coaxial cables 58 and so forth. As described above, since the FPC 56 and at least part of the plurality of coaxial cables 58 are covered with the filling material with high heat release effect and the filling material layer is formed, the ultrasonic vibrator unit 46 of the distal end part 40 of the ultrasonic endoscope 12 according to the present invention, and the portions of the plurality of coaxial cables 58 when the assembly of the ultrasonic observation portion 36 is handled can be protected.

Further, the acoustic impedance of the filling material layer preferably matches the acoustic impedance of the backing material layer 54 so that ultrasonic waves which have been oscillated from the ultrasonic vibrator array 50 and propagated below are not reflected at the boundary with respect to the backing material layer 54, and the ultrasonic waves which have been oscillated from the ultrasonic vibrator array 50 are reflected at the observation target or the periphery thereof and the ultrasonic waves which have propagated below the ultrasonic vibrator array 50 can be sufficiently attenuated.

Further, the acoustic impedance of the filling material layer preferably matches the acoustic impedance of the backing material layer 54. A first reason is that the ultrasonic waves which have oscillated from the ultrasonic vibrator array 50 and propagated below are not reflected at the boundary with respect to the backing material layer 54. A second reason is that the ultrasonic waves which have been oscillated from the ultrasonic vibrator array 50 are reflected at the observation target or the periphery thereof and the ultrasonic waves which have propagated below the ultrasonic vibrator array 50 can be sufficiently attenuated. Hence, when the acoustic impedance of the filling material layer is Zp (kg/m² s) and the acoustic impedance of the backing material layer 54 is Zb (kg/m² s), an acoustic impedance reflectivity Q (%) between the filling material layer and the backing material layer 54 expressed in Expression (1) is preferably 50% or lower.

$$Q = 100 \times |Zp - Zb|/(Zp + Zb) \quad (1)$$

The acoustic impedance reflectivity Q is an index that expresses easiness of reflection of ultrasonic waves (acoustic beams) at the interface between the filling material layer and the backing material layer 54. That is, as the value of the acoustic impedance reflectivity is closer to 0%, this indicates that the acoustic impedance of the filling material layer more closely matches the acoustic impedance of the backing material layer 54. If the acoustic impedance reflectivity is about 50% or lower, the noise caused by the ultrasonic waves which have propagated below the ultrasonic vibrator array 50 can be processed so as not to adversely affect generation of an ultrasound image by the ultrasonic processor device 14 by using the ultrasonic signal received by the ultrasonic vibrator array 50.

Also, when the ultrasonic vibrator array 50 of the ultrasonic vibrator unit 46 oscillates ultrasonic waves, the driving signal transmitted from the ultrasonic processor device 14 to the ultrasonic vibrator array 50 becomes thermal energy.

The ultrasonic vibrator array 50 generates heat due to the thermal energy, and hence the filling material layer preferably has heat release effect. Thus, the filling material layer preferably has a thermal conductivity of 1.0 W/mK or higher.

The ultrasonic observation portion 36 of the distal end part 40 of the ultrasonic endoscope 12 according to the present invention is configured as described above.

The heat release structure 70 of the ultrasonic endoscope 12 according to the first embodiment of the present invention is described with reference to FIG. 5.

As shown in FIG. 5, the heat release structure 70 according to this embodiment consists of a first thermally conductive member according to the present invention, that is, the metal ring 41c that functions as the electrically/thermally conductive member, and an electrically insulating second thermally conductive member that causes the metal ring 41c to be electrically insulated (isolated) from but to be thermally connected to a distal end ring 43a of the angle rings 43 which are the electrically conductive structural bodies of the endoscopic structures. In this case, the distal end ring 43a of the angle rings 43 is a distal-end-side ring of an angle assembly according to the present invention.

As shown in FIG. 5, the heat release structure 70 according to this embodiment consists of the first thermally conductive member according to the present invention, and the second thermally conductive member. The first thermally conductive member according to the present invention is the metal ring 41c that functions as the electrically/thermally conductive member. The second thermally conductive member is the electrically insulating second thermally conductive member that causes the metal ring 41c to be electrically insulated (isolated) from but to be thermally connected to the distal end ring 43a of the angle rings 43 which are the electrically conductive structural bodies of the endoscopic structures. In this case, the distal end ring 43a of the angle rings 43 is the distal-end-side ring of the angle assembly according to the present invention.

According to the present invention, electrically connecting two members represents bringing the two members into direct contact with each other and fixing the two members to each other, or fixing the two members to each other by soldering or by joining the two members with an electrically conductive adhesive or the like, so as to allow electric current to smoothly flow between the two members.

Also, thermally connecting two members represents bringing the two members into direct contact with each other and fixing the two members to each other, or fixing the two members to each other by soldering or by joining the two members with an electrically conductive adhesive or the like, so as to transmit heat between the two members and to allow the heat to be smoothly transmitted from one member to the other member.

With the ultrasonic endoscope 12 according to the present invention, the laminated body 68 of the ultrasonic vibrator unit 46 is directly mounted on and attached to the outer peripheral surface of the cylindrical metal ring 41c in a contact manner. The cylindrical metal ring 41c is inserted into and fitted to an inner hole of the cylindrical backing material layer 54 of the laminated body 68 of the ultrasonic vibrator unit 46. With this configuration, the inner peripheral surface of the backing material layer 54 comes into direct contact with the outer peripheral surface of the metal ring 41c. Consequently, (the plurality of ultrasonic vibrators 48 of) the ultrasonic vibrator array 50 does not have electric continuity with the metal ring 41c, that is, is not electrically connected to the metal ring 41c at the ultrasonic vibrator unit 46. However, heat of the plurality of ultrasonic vibrators 48 and the backing material layer 54 is transmitted to the metal ring 41c.

According to the present invention, the metal ring 41c functions as the cylindrical first thermally conductive member. Further, the metal ring 41c functions as the cylindrical electrically/thermally conductive member.

In this case, the first thermally conductive member according to the present invention preferably has a thermal conductivity of 0.5 W/mK or higher. If the thermal conductivity of the thermally conductive member is lower than 0.5 W/mK, the heat generated from the plurality of ultrasonic vibrators 48 and the backing material layer 54 cannot be efficiently released to the distal end ring 43a which is the endoscopic structure according to the present invention. This may increase the surface temperature of the ultrasonic vibrator unit 46, and may cause a moderate-temperature burn or the like to occur at a body cavity surface.

Note that the metal ring 41c that functions as the first thermally conductive member according to the present invention may use a cylindrical member made of known metal such as SUS.

The first thermally conductive member according to the present invention mentioned herein is, for example, the metal ring 41c.

In the example shown in FIG. 5, since the backing material layer 54 that supports the ultrasonic vibrator array 50 (the plurality of ultrasonic vibrators 48) of the laminated body 68 is in direct contact with the cylindrical metal ring 41c at the ultrasonic vibrator unit 46, the metal ring 41c is not electrically connected to the ultrasonic vibrators 48. That is, this embodiment provides a structure in which, when the metal ring 41c (the first thermally conductive member) is connected to the ultrasonic vibrators 48, the metal ring 41c is insulated from the ultrasonic vibrators 48. However, since the metal ring 41c is disposed closely to the ultrasonic vibrators 48, the withstand voltage is not secured, and hence an electric discharge may occur from the ultrasonic vibrators 48 to the metal ring 41c which is the electrically/thermally conductive member. Owing to this, the ultrasonic vibrators 48 are connected to the metal ring 41c preferably in a state in which electric insulation is secured with respect to the endoscopic structure.

Note that the metal ring 41c is the cylindrical electrically conductive member that supports the ultrasonic vibrator unit 46 at the distal end part 40. Therefore the metal ring 41c is also the cylindrical electrically conductive member that comes into contact with the ultrasonic vibrator array 50 via the backing material layer 54. Also, the metal ring 41c extends from the ultrasonic observation portion 36 of the distal end part 40 toward the distal end ring 43a of the angle rings 43 of the bending part 42. The distal end ring 43a and the metal ring 41c are fixed to each other by a resin screw 104 with the proximal-end-side ring 41b made of a resin interposed therebetween. Hence, the distal end ring 43a is not electrically or thermally connected to the metal ring 41c.

Thus, in this embodiment, heat of the plurality of ultrasonic vibrators 48 and the backing material layer 54 transmitted to the metal ring 41c by heat transmission (heat conduction) is efficiently and safely released to the distal end ring 43a of the angle rings 43 which are the endoscopic structures. Owing to this, the electrically insulating second thermally conductive member (electrically insulating thermally conductive member 102) is interposed between the metal ring 41c which is the first thermally conductive member and the distal end ring 43a of the angle rings 43 which are the endoscopic structures.

In this way, the metal ring 41c is thermally connected to the distal end ring 43a but is electrically insulated or isolated from the distal end ring 43a via the electrically insulating thermally conductive member 102. Thus, the plurality of ultrasonic vibrators 48 and the backing material layer 54 are thermally connected to the distal end ring 43a but are electrically insulated or isolated from the distal end ring 43a via the metal ring 41c which is the first thermally conductive member, and the electrically insulating thermally conductive member 102.

First, the heat generated from the ultrasonic vibrators 48 and the backing material layer 54 of the distal end part 40 is transmitted to the distal end ring 43a of the angle rings 43 which are the endoscopic structures, via the first thermally conductive member (electrically/thermally conductive member) such as the metal ring 41c and the electrically insulating thermally conductive member 102. Further, the heat is transmitted from the distal end ring 43a to the proximal end side of the plurality of angle rings 43 of the bending part 42, and hence the heat can be released to the outside from the operation section 24 through the soft part 44.

Since the metal ring 41c is a component of the ultrasonic vibrator unit 46, the ultrasonic vibrator unit 46 is connected to the distal end ring 43a of the angle rings 43 which are the endoscopic structures, via the electrically insulating thermally conductive member 102.

The electrically insulating thermally conductive member 102 may use any member as long as the member thermally connects the metal ring 41c which is the first thermally conductive member with the distal end ring 43a, and electrically insulates or isolates the metal ring 41c from the distal end ring 43a. The electrically insulating thermally conductive member 102 may use, for example, heat release silicone rubber or a heat release sheet. To have thermal conductivity, a ceramic member, a heat release pad, or an electrically insulating coating, such as diamond-like carbon (DLC) coating or paraffin coating may be used.

The electrically insulating thermally conductive member 102 preferably has a withstand voltage of 1.5 kV or higher. If the withstand voltage of the electrically insulating thermally conductive member 102 is lower than 1.5 kV, the electrically insulating thermally conductive member 102 cannot electrically insulate or isolate the metal ring 41c which is the first thermally conductive member from the distal end ring 43a which is the endoscopic structure. If an electric discharge or an electric leakage occurs at an endoscopic structure due to use of a high-frequency treatment tool or the like, an electric discharge or an electric leakage may occur at the surface of the ultrasonic vibrator unit 46 via the metal ring 41c, thereby possibly applying a burden such as an electric shock to a body cavity surface, or causing a short and hence generating a moderate-temperature burn.

Also, the electrically insulating thermally conductive member 102 preferably has a thermal conductivity of 0.5 W/mK or higher. The reason is similar to the case of the first thermally conductive member because the electrically insulating thermally conductive member 102 is required to transmit the heat generated from the plurality of ultrasonic vibrators 48 and the backing material layer 54 to the distal end ring 43a which is the endoscopic structure according to the present invention, like the metal ring 41c which is the electrically/thermally conductive member.

Also, the electrically insulating thermally conductive member 102 preferably has a thickness of 3 mm or smaller. As long as the electrically insulating thermally conductive member 102 has a thermal conductivity similar to that of the first thermally conductive member, the thickness of the electrically insulating thermally conductive member 102 is not particularly limited. In general, however, the thermal conductivity of the electrically insulating thermally conductive member 102 is lower than that of the first thermally conductive member of the metal ring 41c. In this case, if the thickness of the electrically insulating thermally conductive member 102 is larger than 3 mm, thermal conductivity may be decreased, and the size of the bending part 42 is excessively increased.

With the heat release structure 70 shown in FIG. 5, the metal ring 41c which is the electrically/thermally conductive member and the distal end ring 43a which is the endoscopic structure sandwich the electrically insulating thermally conductive member 102. Thus, the electrically insulating thermally conductive member 102 can be removably disposed on the inner peripheral surface of the distal end ring 43a, thereby improving ease of repair.

While the electrically insulating thermally conductive member 102 is disposed on the inner peripheral surface of the distal end ring 43a in the illustrated example, the electrically insulating thermally conductive member 102 may be disposed on the outer peripheral surface or both inner and outer peripheral surfaces of the distal end ring 43a. Further, when electrically insulating and thermally conductive properties are required, an electrically insulating thermally conductive member is preferably disposed on part of or entirety of the surface of the endoscopic structure.

In the example shown in FIG. 5, the metal ring 41c and the ultrasonic vibrators 48 are disposed closely to each other. Hence, if the withstand voltage is not secured and hence an electric discharge may occur from the ultrasonic vibrators 48 to the metal ring 41c which is the electrically/thermally conductive member, an electrically insulating thermally conductive member similar to the electrically insulating thermally conductive member 102 may be sandwiched between the metal ring 41c and the backing material layer 54.

Alternatively, the electrically insulating thermally conductive member 102 which is the second thermally conductive member may be directly connected to the ultrasonic vibrator array 50. However, the electrically insulating thermally conductive member 102 typically has a lower thermal conductivity than that of a metal ring or the like which is an electrically/thermally conductive member. Hence, if the distance from the electrically insulating thermally conductive member 102 to the endoscopic structure such as the distal end ring 43a is increased, heat is unlikely transmitted to the distal end ring 43a. Thus, the length of the electrically insulating thermally conductive member 102 is preferably as short as possible. To attain this, it is preferable to provide the first electrically conductive member and hence to decrease the distance from the electrically insulating thermally conductive member 102 to the endoscopic structure.

With the heat release structure 70 shown in FIG. 5, the metal ring 41c and the distal end ring 43a sandwich the electrically insulating thermally conductive member 102. However, the present invention is not limited thereto. Like a heat release structure 70a shown in FIG. 8, a ceramic screw 106 that functions as an electrically insulating second thermally conductive member according to the present invention may be used, instead of the resin screw 104 that pinches the electrically insulating thermally conductive member 102 and that fixes the distal end ring 43 a and the metal ring 41c with the proximal-end-side ring 41b interposed therebetween.

Figure 8:
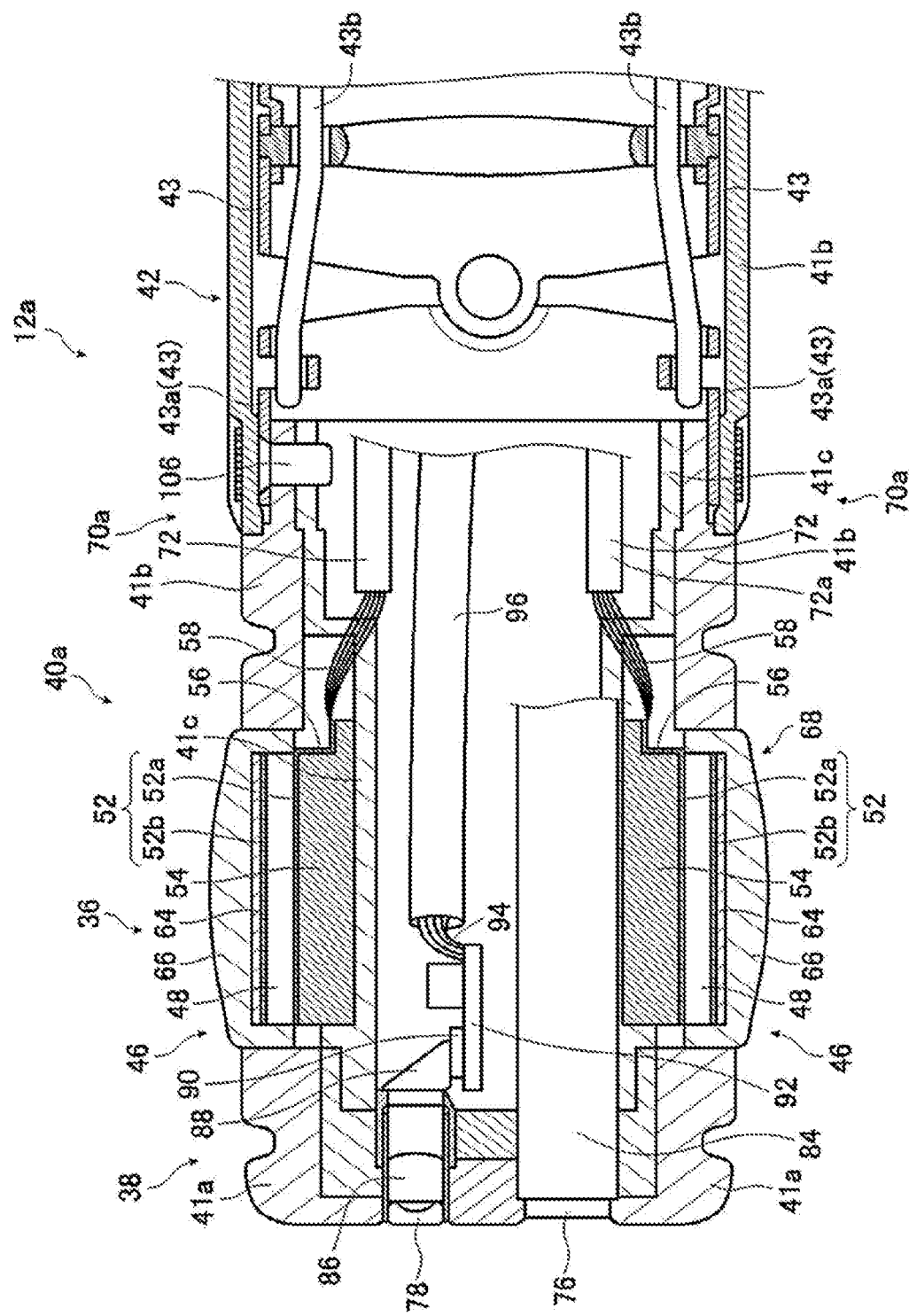
FIG. 8 is a longitudinal section schematically showing another example of a heat release structure of the distal end part of the ultrasonic endoscope shown in FIG. 3.

The heat release structure 70a of a distal end part 40a of an ultrasonic endoscope 12a shown in FIG. 8 consists of the metal ring 41c which is the first thermally conductive member and the ceramic screw 106 which is the electrically insulating second thermally conductive member.

The ceramic screw 106 is inserted through an insertion hole of a distal end ring 43a, screwed into a screw hole of the distal end ring 43a, comes into contact with the distal end ring 43a, and is fastened. The ceramic screw 106 functions as an electrically insulating second thermally conductive member that thermally connects the metal ring 41c which is the first thermally conductive member with the distal end ring 43a. The ceramic screw 106 is removably attached to the distal end ring 43a. Hence, the heat release structure 70a is easily repaired.

The ceramic screw 106 has a withstand voltage and a thermal conductivity similar to those of the electrically insulating thermally conductive member 102.

In this way, the metal ring 41c is thermally connected to the distal end ring 43a via the ceramic screw 106. However, since the metal ring 41c is not open to the endoscopic structure, the metal ring 41c is electrically insulated or isolated from the endoscopic structure.

Thus, the heat release structure 70a shown in FIG. 8 transmits the heat generated from the ultrasonic vibrators 48 and the backing material layer 54 of the distal end part 40a to the distal end ring 43a which is the endoscopic structure, via the first thermally conductive member such as the metal ring 41c, and the ceramic screw 106 that functions as the electrically insulating thermally conductive member. Then, the heat release structure 70a transmits the heat from the bending part 42 to the soft part 44, and can release the heat to the outside from the operation section 24, like the heat release structure 70 shown in FIG. 5.

When a body cavity is observed with the ultrasonic endoscope 12 shown in FIGS. 1 to 7, the insertion section 22 is inserted into the body cavity and searches for an observation target region while an endoscopic optical image acquired by the endoscopic observation portion 38 is observed on the monitor 20.

Then, when the distal end part 40 arrives at the observation target region and an instruction is given to acquire an ultrasonic tomographic image, a driving control signal is input to the ultrasonic vibrators 48 from the ultrasonic processor device 14 via the coaxial cables 58, the FPC 56, and the electrode part 52 in the ultrasonic endoscope 12. When the driving control signal is input, a predetermined voltage is applied to both electrodes of the ultrasonic vibrators 48. Then, the piezoelectric bodies of the ultrasonic vibrators 48 are excited, and emit ultrasonic waves to the observation target region via the acoustic lens 66.

At this time, the ultrasonic vibrators 48 and the backing material layer 54 of the distal end part 40 generate heat. The generated heat is transmitted to the metal ring 41c constituting the heat release structure 70. Then, the heat transmitted to the metal ring 41c is efficiently transmitted to the distal end ring 43a which is the endoscopic structure via the electrically insulating thermally conductive member 102 connected to the metal ring 41c. The heat is transmitted from the distal end ring 43a, to the operation section 24 via the bending part 42 and the soft part 44 of the insertion section 22. Further, the heat transmitted to the operation section 24 is efficiently released to the outside of the body cavity of the subject. Hence, a temperature rise of the distal end part 40 of the ultrasonic endoscope 12 is suppressed, and the ultrasonic endoscope 12 does not give a damage such as a moderate-temperature burn or the like on the body cavity surface with which the distal end part 40 comes into contact. Also, since the electrically insulating thermally conductive member 102 is interposed between the metal ring 41c and the distal end ring 43a, even if an electric discharge or an electric leakage occurs at another endoscopic structure, such as the distal end ring 43a and/or the treatment tool channel (forceps pipe) 84, such an electric discharge or an electric leakage does not flow to the distal end part 40. Therefore, the ultrasonic endoscope 12 according to the present invention does not give a burden due to an electric load on the subject.

In this way, after the observation target region is irradiated with ultrasonic waves, the ultrasonic vibrators 48 receive an echo signal from the observation target region. The irradiation with the ultrasonic waves and the reception of the echo signal are repeated while the ultrasonic vibrator 48 to be driven is shifted by an electronic switch such as a multiplexer. Accordingly, scanning with ultrasonic waves is provided on the observation target region. With the ultrasonic processor device 14, an ultrasonic tomographic image is generated based on a detection signal that is output from the ultrasonic vibrators 48 using the echo signal received by the ultrasonic vibrators 48. The generated ultrasonic tomographic image is displayed on the monitor 20.

Note that even when the heat release structure 70a shown in FIG. 8 is used, an ultrasonic tomographic image can be obtained likewise.

The ultrasonic endoscope according to the first embodiment of the present invention is configured as described above.

With the heat release structures 70 and 70a shown in FIGS. 5 and 8, the distal end ring 43a of the angle rings 43 serves as the electrically conductive structural body which is the endoscopic structure, and the metal ring 41c serves as the first thermally conductive member. However, the present invention is not limited thereto, and an electrically conductive structural body may serve as another endoscopic structure, or a thermally conductive member may be additionally provided.

Figure 9:
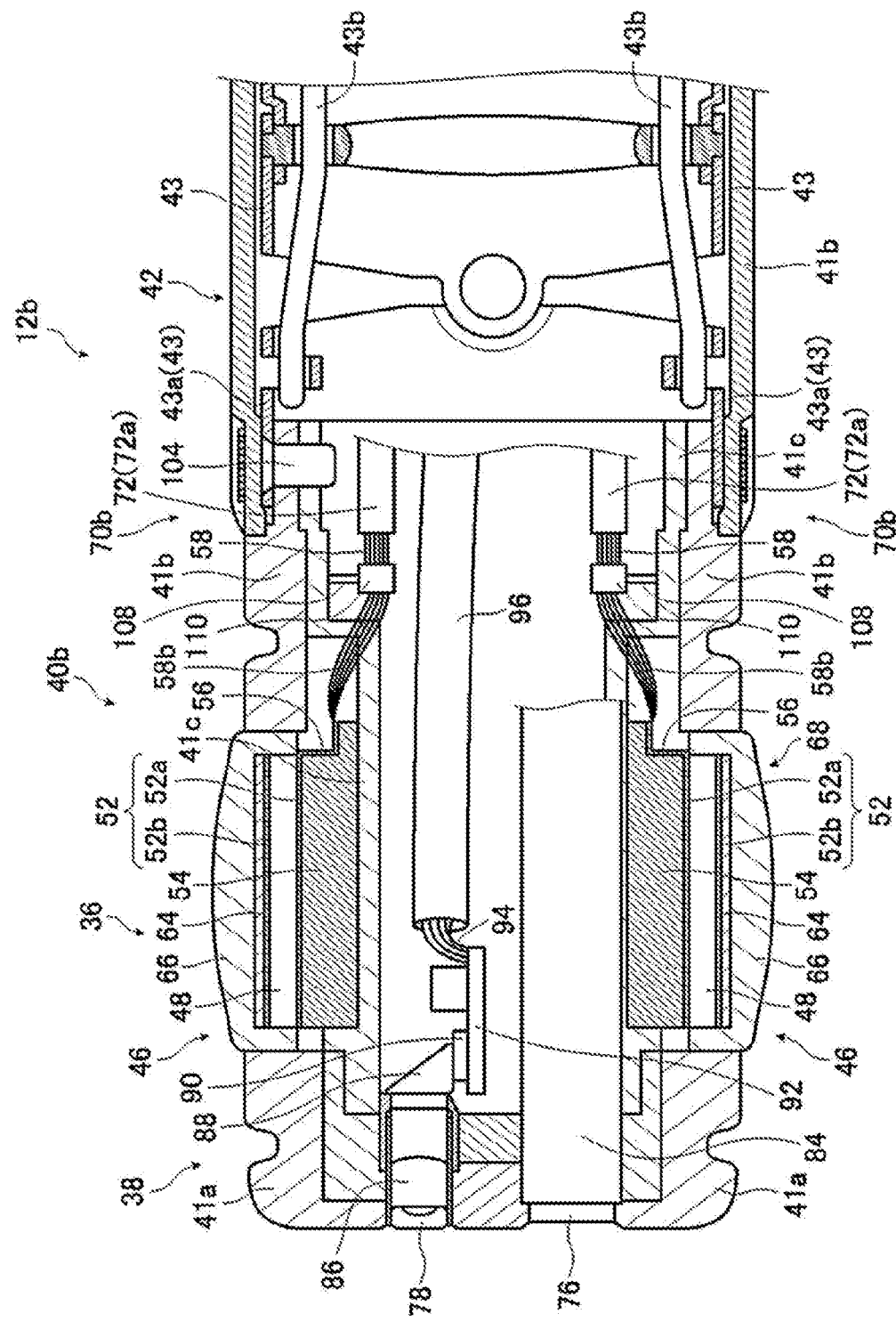
FIG. 9 is a longitudinal section schematically showing still another example of a heat release structure of the distal end part of the ultrasonic endoscope shown in FIG. 3.

Heat release structures according to other various embodiments are described below with reference to FIGS. 9 and 12. FIGS. 9 to 12 emphasize members relating to the heat release structures and so forth like FIG. 5 to explain the heat release structures of the ultrasonic endoscopes according to the other various embodiments. Hence, FIGS. 9 to 12 are drawings that emphasize the part required for the explanation, whereas simplify or omit the part not used for the explanation.

Second Embodiment

FIG. 9 is a partial section schematically showing an example of a distal end part of an ultrasonic endoscope according to a second embodiment of the present invention.

A distal end part 40b of an ultrasonic endoscope 12b shown in FIG. 9 has an integrated ground 110 at the plurality of coaxial cables 58, as an electrically conductive structural body which is an endoscopic structure. The distal end part 40b of the ultrasonic endoscope 12b shown in FIG. 9 has a configuration similar to that of the distal end part 40 of the ultrasonic endoscope 12 shown in FIG. 5 except for the following different point, and therefore the same reference sign is applied to the same component and the redundant description is omitted. A different point is that the ultrasonic vibrator unit 46 is thermally connected to the integrated ground 110 via a second thermally conductive member 108. For example, a different point is that the ultrasonic vibrator array 50 is thermally connected to the integrated ground 110 via the metal ring 41c which is the first thermally conductive member, and the second thermally conductive member 108.

A heat release structure 70b of the distal end part 40b of the ultrasonic endoscope 12b shown in FIG. 9 includes the integrated ground 110 which is an electrically conductive structural body of an endoscopic structure, the metal ring 41c which is the first thermally conductive member, and the second thermally conductive member 108 that thermally connects the metal ring 41c with the integrated ground 110. In this case, the metal ring 41c which is the first thermally conductive member, and the second thermally conductive member 108 constitute a thermally conductive member according to the present invention.

The integrated ground 110 is a bundle of the plurality of coaxial cables 58 of the shield cable 72 using a metal ring-shaped body in a manner that the shield members 58c of the coaxial cables 58 are in close contact with one another. All the shield members 58c and the metal ring-shaped body are electrically/thermally connected to one another.

Note that at the integrated ground 110, the shield members 58c of the plurality of coaxial cables 58 serve as outer surfaces of the coaxial cables 58. Distal ends that are connected to the plurality of connection portions of the FPC 56 are only the signal lines 58a. In an area between the integrated ground 110 and the plurality of connection portions of the FPC 56, the first insulating layers 58b serve as the outer surfaces. Each signal line 58a is covered with the first insulating layer 58b. The plurality of signal lines 58a are insulated from one another.

The second thermally conductive member 108 is not particularly limited as long as the second thermally conductive member 108 can transmit heat which has been generated from the plurality of ultrasonic vibrators 48 and the backing material layer 54 and has been transmitted to the metal ring 41c, to the integrated ground 110. The second thermally conductive member 108 may be any member as long as the member has thermal conductivity and can be flexibly housed in a narrow space of the distal end part 40b of the ultrasonic endoscope 12b. Since the second thermally conductive member 108 is required to have thermal conductivity and to be flexibly housed in a narrow space, for example, a thermally conductive cable such as a cable having a core wire, a thermally conductive wire material such as a metal wire, or a thermally conductive net such as a metal net member may be used.

When such a thermally conductive member is used as the second thermally conductive member 108, to increase thermal transmission efficiency, it is preferable to use a cable including a core wire thicker than the signal line 58a of each coaxial cable 58, or a metal wire thicker than the signal line 58a.

When flexibility is desired for the second thermally conductive member 108 so as to be housed in a narrow space, it is preferable to use a metal-bladed net member.

Further, by using an electrically insulating thermally conductive member as the second thermally conductive member 108, resistance to noise can be increased. The electrically insulating thermally conductive member may use, for example, heat release silicone rubber or a heat release sheet.

Note that the heat release structure 70b according to the second embodiment shown in FIG. 9 may use the electrically insulating thermally conductive member 102 or the ceramic screw 106, like the heat release structures 70 and 70a according to the first embodiment shown in FIGS. 5 and 8.

The heat release structure 70b according to this embodiment first transmits the heat generated from the ultrasonic vibrators 48 and the backing material layer 54 of the distal end part 40b to the integrated ground 110 which is the endoscopic structure, via the first thermally conductive member such as the metal ring 41c, and the second thermally conductive member 108. Then, the heat of the integrated ground 110 is released to the shield members 58c of the plurality of coaxial cables 58, transmitted from the bending part 42 to the soft part 44 and the operation section 24, and released from the universal cord 26 to the outside.

Third Embodiment

Figure 10:
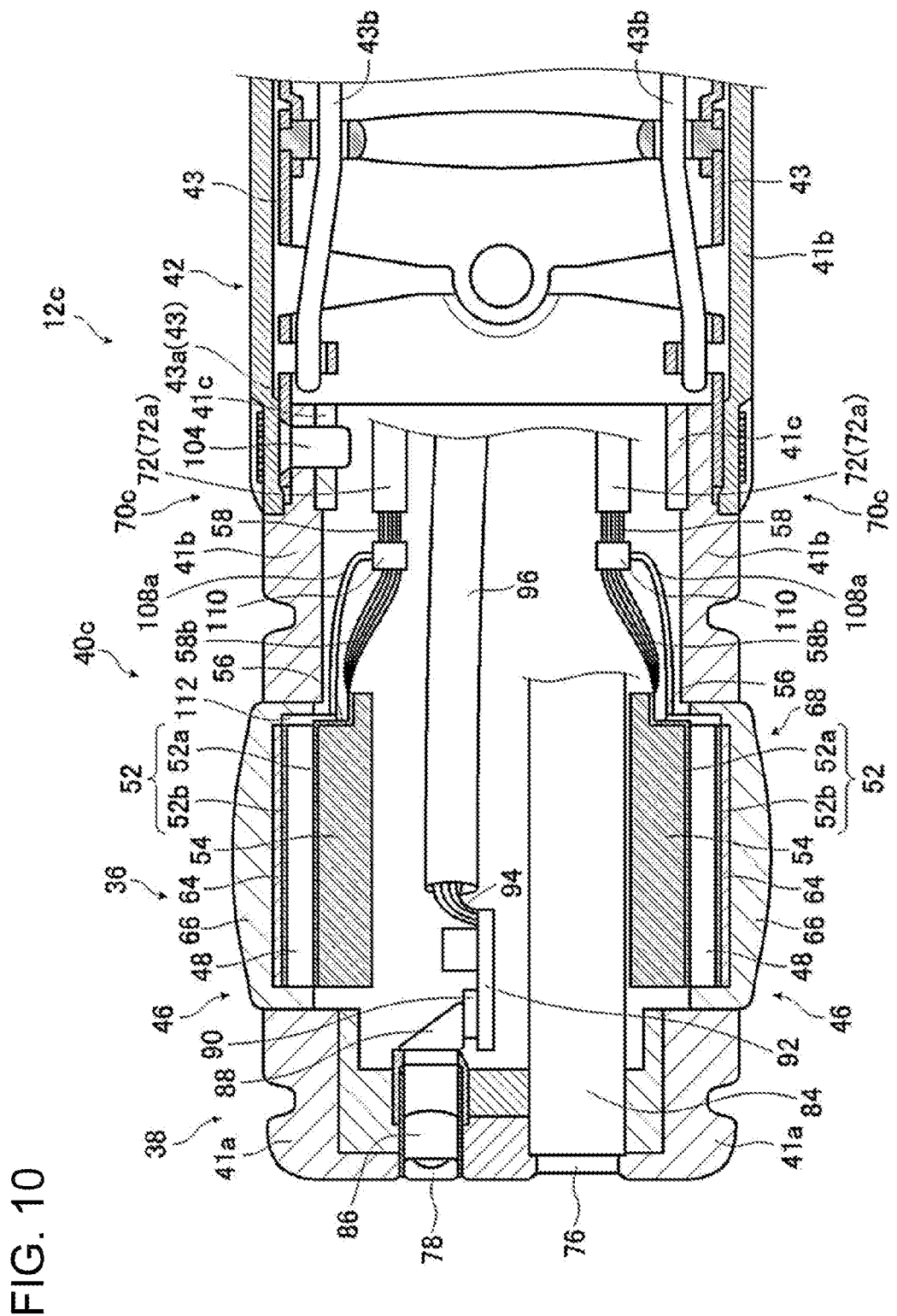
FIG. 10 is a longitudinal section schematically showing yet another example of a heat release structure of the distal end part of the ultrasonic endoscope shown in FIG. 3.

FIG. 10 is a partial section schematically showing an example of a distal end part of an ultrasonic endoscope according to a third embodiment of the present invention.

A distal end part 40c of an ultrasonic endoscope 12c shown in FIG. 10 has a configuration similar to that of the distal end part 40b of the ultrasonic endoscope 12b shown in FIG. 9 except for the following different point, and therefore the same reference sign is applied to the same component and the redundant description is omitted. For example, a different point is that a copper foil 112 is provided instead of the metal ring 41c as a first thermally conductive member of a thermally conductive member, and the ultrasonic vibrator array 50 of the ultrasonic vibrator unit 46 is thermally connected to the integrated ground 110 via the copper foil 112 which is the first thermally conductive member of the thermally conductive member, and a second thermally conductive member 108a.

A heat release structure 70c of the distal end part 40c of the ultrasonic endoscope 12c shown in FIG. 10 includes the integrated ground 110, the copper foil 112 which is the first thermally conductive member, and the second thermally conductive member 108a that thermally connects the copper foil 112 and the integrated ground 110 to each other. In this case, the copper foil 112 which is the first thermally conductive member, and the second thermally conductive member 108a constitute a thermally conductive member according to the present invention.

As shown in FIG. 10, the copper foil 112 is a thermally conductive member that is directly connected to the plurality of ultrasonic vibrators 48. The copper foil 112 is bonded to the plurality of ultrasonic vibrators 48 and a side surface on the proximal end side of the backing material layer 54, further extends toward the proximal end side, and is connected to the integrated ground 110. The copper foil 112 shields the plurality of ultrasonic vibrators 48 and also releases the heat generated from the plurality of ultrasonic vibrators 48 and the backing material layer 54 to the integrated ground 110.

The copper foil 112 constitutes the heat release structure 70c together with the second thermally conductive member 108a. The copper foil 112 is bonded to the plurality of ultrasonic vibrators 48 of the ultrasonic vibrator array 50, and is disposed on at least a side surface of the ultrasonic vibrator array 50, that is, an end surface on the proximal end side of the laminated body 68. More specifically, the copper foil 112 is disposed on end surfaces on the proximal end side of the ultrasonic vibrator array 50 and the backing material layer 54.

Connection of the copper foil 112 to the plurality of ultrasonic vibrators 48 may be performed by bonding the copper foil 112 to outer side surfaces of the ultrasonic vibrator array 50 and the backing material layer 54. The copper foil 112 is bonded preferably by using an electrically conductive member, such as solder, silver paste, or an electrically conductive adhesive, or a silicone-based electrically non-conductive adhesive.

The copper foil 112 is not limited to the foil form, and preferably has a shape, such as a mesh form or a sheet form, that can sufficiently transmit heat from the side surfaces in the width direction of the ultrasonic vibrator array 50 and the backing material layer 54.

While the copper foil 112 is used as the thermally conductive member according to the present invention, for example, the first thermally conductive member, the present invention is not limited thereto, and may use any member as long as the member has high thermal conductivity. For example, in case of a thin plate-shaped body, a metal foil, such as an aluminum foil, a gold foil, or a silver foil may be used. Alternatively, a metal sheet such as a sheet metal, for example, a copper sheet may be used. Further alternatively, without limiting to a thin plate-shaped body, a member that can be used as an electrically/thermally conductive member, for example, a metal-bladed net member, a metal mesh, or a cable having a thicker core wire than that of the signal line 58a of each coaxial cable 58 may be used.

Also, while the copper foil 112 is directly connected to the plurality of ultrasonic vibrators 48 in the illustrated example, the present invention is not limited thereto. The copper foil 112 may be connected to a substrate fixed to the plurality of ultrasonic vibrators 48, and/or a heat release plate.

With the ultrasonic vibrator unit 46 shown in FIG. 10, the heat release structure 70c having the copper foil 112 is provided on only one side surface of the laminated body 68 (the plurality of ultrasonic vibrators 48 and the backing material layer 54). However, the present invention is not limited thereto. The heat release structure 70c having the copper foil 112 may be provided on both side surfaces of the laminated body 68.

The heat release structure 70c according to this embodiment first transmits the heat generated from the ultrasonic vibrators 48 and the backing material layer 54 of the distal end part 40c to the integrated ground 110 which is the endoscopic structure, via the first thermally conductive member such as the copper foil 112, and the second thermally conductive member 108a. Then, the heat release structure 70c according to this embodiment releases the heat of the integrated ground 110 to the shield members 58c of the plurality of coaxial cables 58, like the heat release structure 70b shown in FIG. 9. Further, the heat release structure 70c according to this embodiment transmits the heat released to the shield members 58c, from the bending part 42 to the soft part 44 and the operation section 24, and released from the universal cord 26 to the outside.

Figure 11:
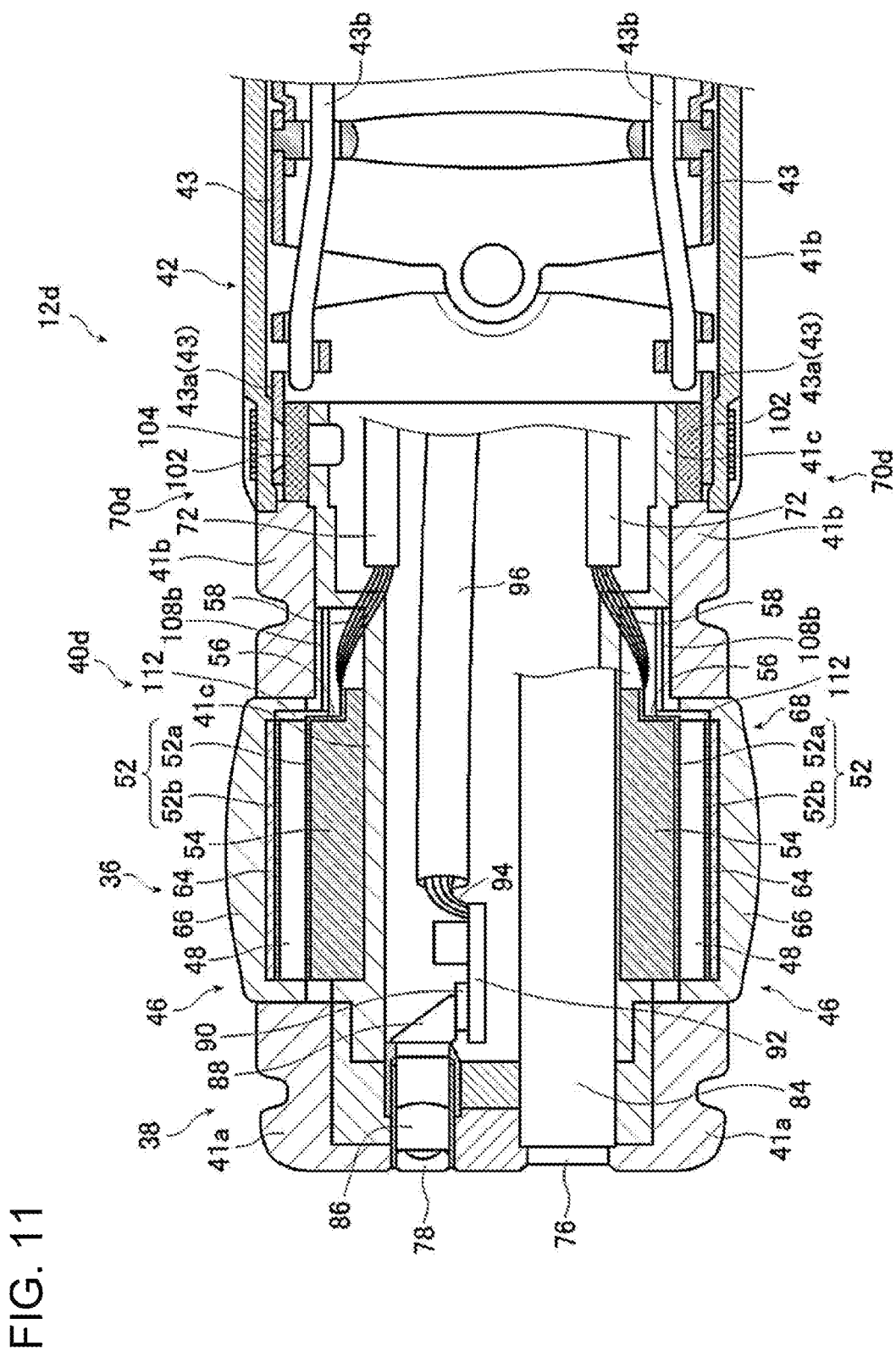
FIG. 11 is a longitudinal section schematically showing a further example of a heat release structure of the distal end part of the ultrasonic endoscope shown in FIG. 3.
Figure 12:
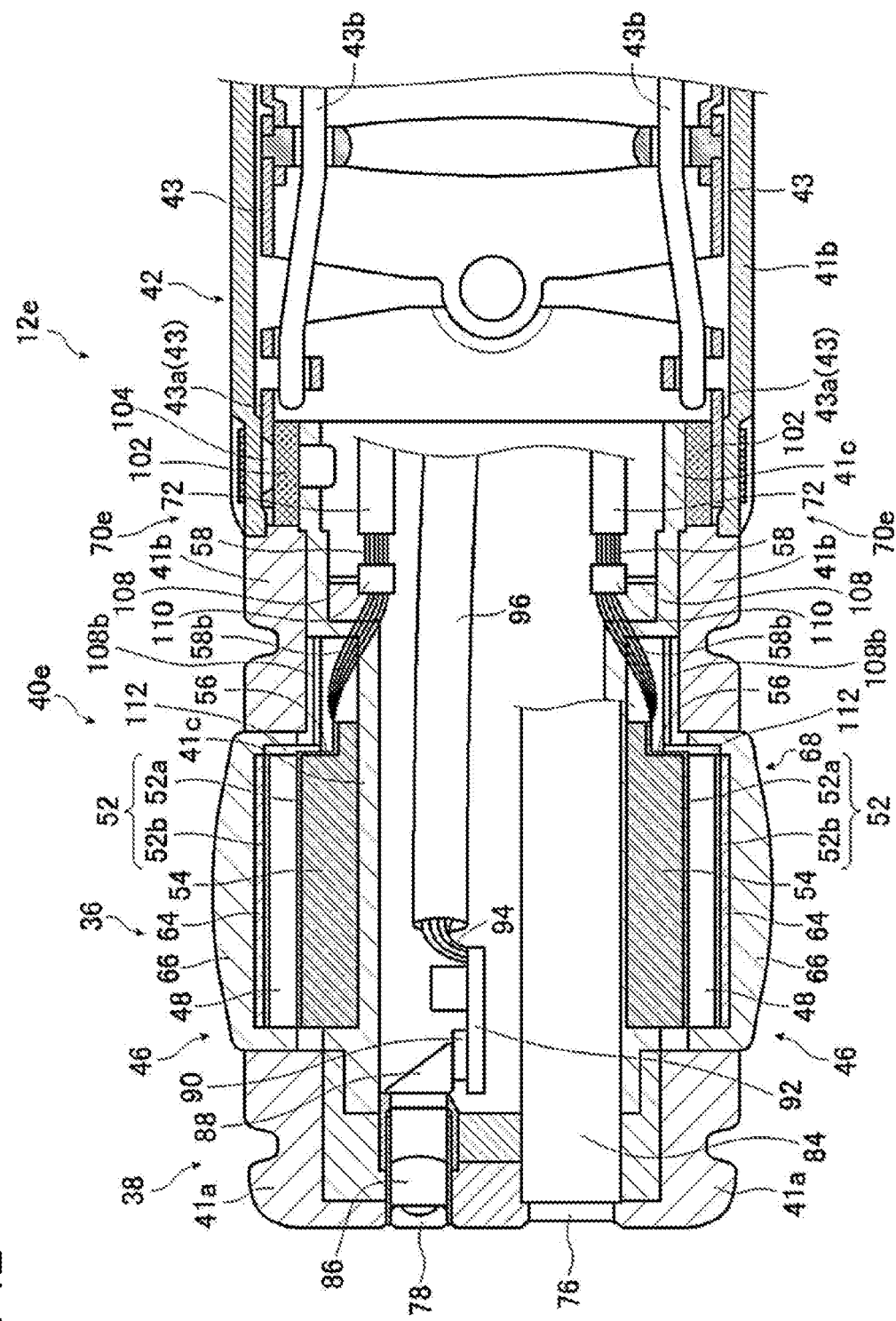
FIG. 12 is a longitudinal section schematically showing a still further example of a heat release structure of the distal end part of the ultrasonic endoscope shown in FIG. 3.

FIG. 11 is a partial section schematically showing another example of a distal end part of an ultrasonic endoscope according to the third embodiment of the present invention.

A distal end part 40d of an ultrasonic endoscope 12d shown in FIG. 11 has a configuration similar to that of the distal end part 40c of the ultrasonic endoscope 12c shown in FIG. 10 except for the following different points, and therefore the same reference sign is applied to the same component and the redundant description is omitted. A different point is that a second thermally conductive member 108b, the metal ring 41c, and the electrically insulating thermally conductive member 102 are further provided in addition to the copper foil 112. Further, another different point is that the ultrasonic vibrator array 50 of the ultrasonic vibrator unit 46 is thermally connected to the distal end ring 43a of the angle rings 43 via the copper foil 112, the second thermally conductive member 108b, the metal ring 41c, and the second thermally conductive member 102.

A heat release structure 70d of the distal end part 40d of the ultrasonic endoscope 12d shown in FIG. 11 includes the distal end ring 43a of the angle rings 43, the copper foil 112, the second thermally conductive member 108b that thermally connects the copper foil 112 with the metal ring 41c, and the electrically insulating thermally conductive member 102 that connects the metal ring 41c with the distal end ring 43a. In this case, the copper foil 112, the second thermally conductive member 108b, and the metal ring 41c constitute a thermally conductive member according to the present invention.

That is, this embodiment provides a structure in which, when the metal ring 41c is connected to the ultrasonic vibrators 48, the metal ring 41c has electric continuity with the ultrasonic vibrators 48. With this structure, by connecting the copper foil 112 with the ground of the ultrasonic vibrators 48 and by connecting the copper foil 112 with the metal ring 41c, the ground of the ultrasonic vibrator 48 is connected to the electrically conductive first thermally conductive member.

With the heat release structure 70d according to this embodiment, the copper foil 112 is connected to the ultrasonic vibrators 48 and the backing material layer 54 of the distal end part 40d. Then, the copper foil 112 and the metal ring 41c are thermally connected with each other by the second thermally conductive member 108b. Further, the metal ring 41c is thermally connected to the distal end ring 43a by the electrically insulating thermally conductive member 102, and hence electrically insulating the metal ring 41c from the distal end ring 43a, like the first embodiment.

In this way, the heat generated from the ultrasonic vibrators 48 and the backing material layer 54 is transmitted to the thermally conductive member according to the present invention consisting of the first thermally conductive member, the second thermally conductive member 108b, and the first thermally conductive member. Then, the transmitted heat is released to the distal end ring 43a by using the electrically insulating thermally conductive member 102. Further, the heat of the distal end ring 43a is successively transmitted to the plurality of angle rings 43, and is transmitted from the bending part 42 to the soft part 44, like the heat release structures 70 and 70a shown in FIGS. 5 and 8. Finally, the heat transmitted to the soft part 44 can be released to the outside from the operation section 24.

Note that this embodiment uses the electrically insulating thermally conductive member 102, like the first embodiment shown in FIG. 5. However, this embodiment may use the ceramic screw 106 shown in FIG. 8 that functions as an electrically insulating thermally conductive member, instead of the electrically insulating thermally conductive member 102.

The copper foil 112 is a first thermally conductive member of a thermally conductive member. Also, the metal ring 41c functions as another first thermally conductive member, like the first embodiment.

FIG. 12 is a partial section schematically showing still another example of a distal end part of an ultrasonic endoscope according to the third embodiment of the present invention.

A distal end part 40e of an ultrasonic endoscope 12e shown in FIG. 12 has a configuration similar to that of the distal end part 40c of the ultrasonic endoscope 12c shown in FIG. 11 except for the following different points, and therefore the same reference sign is applied to the same component and the redundant description is omitted. The distal end part 40e of the ultrasonic endoscope 12e shown in FIG. 12 has the integrated ground 110 at the plurality of coaxial cables 58, as an electrically conductive structural body which is an endoscopic structure. Another different point is that the ultrasonic vibrator unit 46 is thermally connected to the integrated ground 110 via a thermally conductive member. The thermally conductive member mentioned herein is, for example, the metal ring 41c which is the first thermally conductive member, and the second thermally conductive member 108.

A heat release structure 70e of the distal end part 40e of the ultrasonic endoscope 12e shown in FIG. 12 includes, as endoscopic structures, the distal end ring 43a of the angle rings 43 and the integrated ground 110; and further includes the copper foil 112, the second thermally conductive member 108b, the electrically insulating thermally conductive member 102, and another second thermally conductive member 108. The second thermally conductive member 108b thermally connects the copper foil 112 with the metal ring 41c. The electrically insulating thermally conductive member 102 connects the metal ring 41c with the distal end ring 43a. The other second thermally conductive member 108 connects the metal ring 41c with the integrated ground 110.

The copper foil 112, the second thermally conductive member 108b, the metal ring 41c, and the other second thermally conductive member 108 constitute a thermally conductive member according to the present invention.

With the heat release structure 70e of the distal end part 40e of the ultrasonic endoscope 12e shown in FIG. 12, the copper foil 112, the second thermally conductive member 108b, the electrically insulating thermally conductive member 102, the metal ring 41c, and the distal end ring 43a have the same configurations as those of the heat release structure 70d shown in FIG. 11. Further, with the heat release structure 70e of the distal end part 40e of the ultrasonic endoscope 12e shown in FIG. 12, the metal ring 41c and the integrated ground 110 have the same configurations as those of the heat release structure 70b shown in FIG. 9.

Thus, the heat release structure 70e shown in FIG. 12 has a configuration in which the heat release structure 70d shown in FIG. 11 and the heat release structure 70b shown in FIG. 9 are combined, has combined functions thereof, and attains combined effects thereof.

Note that the heat release structure 70e according to the third embodiment shown in FIG. 12 may use the ceramic screw 106, instead of the electrically insulating thermally conductive member 102, like the heat release structures 70 and 70a according to the first embodiment shown in FIGS. 5 and 8.

With the heat release structure 70e according to this embodiment, the heat generated from the ultrasonic vibrators 48 and the backing material layer 54 of the distal end part 40e is transmitted to the thermally conductive member according to the present invention. Then, with the heat release structure 70e according to this embodiment, the transmitted heat is released to the distal end ring 43a by using the electrically insulating thermally conductive member 102. Further, with the heat release structure 70e according to this embodiment, the heat of the distal end ring 43a is successively transmitted to the plurality of angle rings 43, is transmitted from the bending part 42 to the soft part 44, and can be released to the outside from the operation section 24, like the heat release structures 70 and 70a shown in FIGS. 5 and 8. Further, the heat release structure 70e according to this embodiment transmits the heat generated from the ultrasonic vibrators 48 and the backing material layer 54 of the distal end part 40e to the integrated ground 110 which is the endoscopic structure, via the first thermally conductive member such as the metal ring 41c, and the second thermally conductive member 108. Then, the heat of the integrated ground 110 is released to the shield members 58c of the plurality of coaxial cables 58, transmitted from the bending part 42 to the soft part 44 and the operation section 24, and released from the universal cord 26 to the outside.

Note that, in this case, the thermally conductive member according to the present invention consists of the first thermally conductive member such as the copper foil 112, the second thermally conductive member 108b, and another first thermally conductive member such as the metal ring 41c.

The ultrasonic endoscope according to the present invention has been described above in detail with reference to various embodiments and various examples; however, the invention is not limited to the above-described embodiments and examples, and as the matter of course the embodiments and examples may be improved and modified in various ways within the scope of the invention.

REFERENCE SIGNS LIST 10 ultrasonic inspection system
12, 12a, 12b, 12c, 12d, 12e ultrasonic endoscope
14 ultrasonic processor device
16 endoscopic processor device
18 light source device
20 monitor
21a water supply tank
21b suction pump
22 insertion section
24 operation section
26 universal cord
28a air/water supply button
28b suction button
29 angle knob
30 treatment tool insertion port (forceps port)
32a ultrasonic connector
32b endoscope connector
32c light source connector
34a air/water supply tube
34b suction tube
36 ultrasonic observation portion
38 endoscopic observation portion
40, 40a, 40b, 40c, 40d, 40e distal end part
41a distal end component
41b proximal end ring
41c metal ring (first thermally conductive member)
42 bending part
43 angle ring
43a distal end ring
43b operating wire
44 soft part
46 ultrasonic vibrator unit
48 ultrasonic vibrator (transducer)
50 ultrasonic vibrator array
52 electrode part
52a individual electrode
52b common electrode
54 backing material layer
56 flexible printed circuit (FPC)
58 coaxial cable
58a signal line
58b first insulating layer
58c shield member
58d second insulating layer
64 acoustic matching layer
66 acoustic lens
68 laminated body
70, 70a, 70b, 70c, 70d, 70e heat release structure 72, 96 shield cable
72a outer cover
76 treatment tool lead-out port (forceps lead-out port)
78 observation window
80 illumination window
82 washing (air/water supply) nozzle
84 treatment tool channel (forceps pipe line)
86 objective lens
88 prism
90 solid-state imaging element
92 substrate
94 wiring cable
98 light guide
100 air/water supply channel (pipe line)
102 electrically insulating thermally conductive member
104 screw
106 ceramic screw
108, 108a, 108b second thermally conductive member
110 integrated ground
112 copper foil (first thermally conductive member)
EL longitudinal direction (elevation direction)
AZ parallel direction (azimuth direction)

What is claimed is:

1. An ultrasonic endoscope comprising:
    a distal end part having an ultrasonic vibrator array including a plurality of ultrasonic vibrators; and
    a bending part being connected to a proximal end side of the distal end part, said bending part being formed by an angle assembly having an angle ring structure in which a plurality of angle rings are pivotally connected to one another in an axial direction, and being bendable,
    wherein the distal end part comprises an ultrasonic vibrator unit being composed of at least the ultrasonic vibrator array, a backing material layer supporting the ultrasonic vibrator array, and a first thermally conductive member,
    wherein the ultrasonic endoscope further comprises:
    a plurality of cables that are electrically connected to the ultrasonic vibrator array;
    an electrically conductive structural body that is disposed to extend from a distal end side toward a proximal end side of the ultrasonic endoscope; and
    an electrically insulating second thermally conductive member connecting the first thermally conductive member to the electrically conductive structural body,
    wherein the first thermally conductive member is a cylindrical and electrically conductive member, houses a shield cable which covers the plurality of cables at an inside of the first thermally conductive member, and connects the ultrasonic vibrator unit to the electrically insulating second thermally conductive member,
    wherein the ultrasonic vibrator array has the plurality of ultrasonic vibrators that are arranged in a cylindrical form on the outer peripheral surface of the backing material layer having a cylindrical shape,
    wherein the electrically conductive structural body is a distal-end-side ring component of the angle assembly, and
    wherein heat of the plurality of ultrasonic vibrators and the backing material layer is transmitted to the first thermally conductive member and the electrically insulating second thermally conductive member in this order, and further to a proximal end side of the angle assembly through the distal-end-side ring component, and then released to the outside of the ultrasonic endoscope.

2. The ultrasonic endoscope according to claim 1, wherein the second thermally conductive member is removably connected to the first thermally conductive member or the electrically conductive structural body.

3. The ultrasonic endoscope according to claim 1, wherein the second thermally conductive member has a withstand voltage of 1.5 kV or higher.

4. The ultrasonic endoscope according to claim 1, wherein the second thermally conductive member has a thickness of 3 mm or smaller.

5. The ultrasonic endoscope according to claim 1, wherein the second thermally conductive member has a thermal conductivity of 0.5 W/mK or higher.

6. The ultrasonic endoscope according to claim 1, wherein the second thermally conductive member is a ceramic member, a heat release sheet, a heat release pad, or an electrically insulating coating.

7. The ultrasonic endoscope according to claim 1, wherein the second thermally conductive member is a ceramic screw.

8. The ultrasonic endoscope according to claim 1,
    wherein the distal end part has a forceps lead-out port, and
    wherein the forceps lead-out port is disposed on a distal end side with respect to the plurality of ultrasonic vibrators.

9. The ultrasonic endoscope according to claim 1, wherein the plurality of ultrasonic vibrators are radial type.

10. The ultrasonic endoscope according to claim 1, further comprising:
    a copper foil being bonded to the plurality of ultrasonic vibrators and a side surface on a proximal end side of the backing material layer; and
    a thermally conductive member connecting the copper foil to the first thermally conductive member,
    wherein the heat of the plurality of ultrasonic vibrators and the backing material layer is further transmitted to the copper foil and the thermally conductive member in this order and then to the first heat conductive member.

* * * * *